United States Patent
Hoener et al.

(10) Patent No.: US 10,092,546 B2
(45) Date of Patent: *Oct. 9, 2018

(54) IMIDAZOLE DERIVATIVES

(71) Applicant: Hoffman-La Roche Inc., Little Falls, NJ (US)

(72) Inventors: Marius Hoener, Basel (CH); Juergen Wichmann, Steinen (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,444

(22) Filed: Jan. 9, 2018

(65) Prior Publication Data

US 2018/0125823 A1    May 10, 2018

Related U.S. Application Data

(63) Continuation of application No. PCT/EP2016/066388, filed on Jul. 11, 2016.

(30) Foreign Application Priority Data

Jul. 14, 2015 (EP) .................................. 15176652

(51) Int. Cl.
| | |
|---|---|
| *A61K 31/4178* | (2006.01) |
| *C07D 401/04* | (2006.01) |
| *C07D 409/14* | (2006.01) |
| *A61P 25/30* | (2006.01) |
| *A61P 25/18* | (2006.01) |
| *C07B 43/04* | (2006.01) |
| *C07D 403/04* | (2006.01) |

(52) U.S. Cl.
CPC .......... *A61K 31/4178* (2013.01); *A61P 25/18* (2018.01); *A61P 25/30* (2018.01); *C07B 43/04* (2013.01); *C07D 401/04* (2013.01); *C07D 403/04* (2013.01); *C07D 409/14* (2013.01); *C07B 2200/07* (2013.01)

(58) Field of Classification Search
CPC . A61K 31/4178; C07D 403/04; C07D 409/14
USPC ........................................................ 514/341
See application file for complete search history.

(56) References Cited

FOREIGN PATENT DOCUMENTS

| WO | 2010/033168 A2 | 3/2010 |
| WO | 2010/051188 A1 | 6/2010 |
| WO | WO2017009274 A1 * | 1/2017 |

OTHER PUBLICATIONS

George Patani , Bioisosterism (Year: 1996).*
Andres Jensen , Excitory amino acid transporters (Year: 2015).*
Larissa Jarzylo et al , Parasynaptic NMDA receptor Signaling Couples Neuronal Glutamate Transpoter Function to AMPA Receptor Synaptic Distribution and Stability. (Year: 2012).*
Robert McCullumsmith et al , Striatal Excitatory Amino Acid Transporter Transcript Expression in Schizophrenia, Bipolar Disorder and major Depressive Disorder. (Year: 2002).*
ISR of PCT/EP2016/066388 (dated Sep. 5, 2016).

* cited by examiner

*Primary Examiner* — Rita J Desai
(74) *Attorney, Agent, or Firm* — Brian L. Buckwalter

(57) ABSTRACT

The present invention relates to compounds of formula I

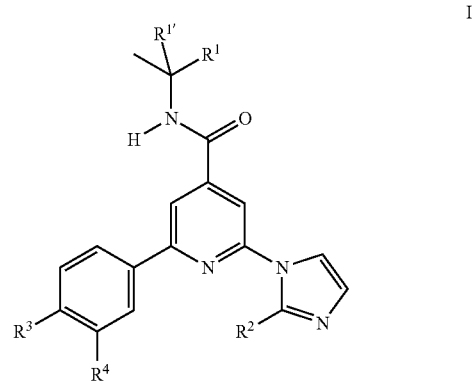

wherein
$R^{1'}$ is $CH_3$;
$R^1$ is methyl, ethyl, $CF_3$, $CH_2OH$, cyclopropyl or cyano, or $R^{1'}$ and $R^1$ may form together a 1,1-dioxo-tetrahydro-thiophen-3-yl ring;
$R^2$ is hydrogen, methyl, ethyl, isopropyl, tertbutyl, cyclopropyl, hydroxmethyl, or 2-propyl-2-ol;
$R^3$ is Cl, F, $CF_3$, methyl, methoxy, isopropyl, cyano or cyclopropyl;
$R^4$ is hydrogen, methyl, F or Cl;

or to a pharmaceutically acceptable salt or acid addition salt, to a racemic mixture, or to its corresponding enantiomer and/or optical isomer and/or stereoisomer thereof.

The compounds of formula I may be used in the treatment of psychiatric disorders such as schizophrenia, bipolar disorder, obsessive-compulsive disorder or autism spectrum disorder.

18 Claims, No Drawings

IMIDAZOLE DERIVATIVES

CROSS REFERENCE TO RELATED APPLICATIONS

This application is a continuation of International Application No. PCT/EP2016/066308 having an international filing date of Jul. 11, 2016 and which claims benefit under 35 U.S.C. § 119 to European Patent Application No. 15176652.4 having an international filing date of Jul. 14, 2015. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

The excitatory amino acid transporter 3 (EAAT3), also referred to in human studies as solute carrier family 1, member 1 (systematic gene name: SLC1A1) and in rodents as excitatory amino acid carrier 1 (EAAC1), is a high-affinity anionic amino acid transporter found in neurons throughout the cortex and in the hippocampus, basal ganglia (striatum, thalamus), and the olfactory bulb. EAAT3 functions to buffer local glutamate concentrations at excitatory synapses, for example in the hippocampus, and modulates the differential recruitment of glutamate receptor subtypes at extrasynaptic sites. Furthermore, EAAT3 is thought to be involved in facilitating GABA and glutathione biosynthesis. EAAT3 is a member of the EAAT family that mediates the uptake of glutamate into neuronal and glial cells of the mammalian CNS. Two transporters expressed primarily in glia, EAAT1 and EAAT2, are crucial for glutamate homeostasis in the adult mammalian brain and for rapid clearance of glutamate from the synaptic cleft. Three neuronal transporters (EAAT3, EAAT4, and EAAT5) appear to have additional functions in regulating and processing cellular excitability with EAAT3 being abundantly expressed throughout the CNS (EAAT4 is unique to Purkinje cells of the cerebellum and EAAT5 is expressed in rod photoreceptor and bipolar cells of the retina).
EAATs are assembled as trimers, and the existence of multiple isoforms raises the question of whether certain isoforms can form hetero-oligomers. In the mammalian brain, the specificity of excitatory synaptic transmission depends on rapid diffusion of glutamate away from active synapses and the powerful uptake capacity of glutamate transporters in astrocytes. The extent to which neuronal glutamate transporters influence the lifetime of glutamate in the extracellular space remains unclear, but it is thought to be minor. EAAT3, the predominant neuronal glutamate transporter at excitatory synapses in hippocampal area CA1, buffers glutamate released during synaptic events and prolongs the time course of its clearance by astrocytes. EAAT3 does not significantly alter activation of receptors in the synaptic cleft. Instead, it reduces recruitment of perisynaptic/extrasynaptic NR2B-containing NMDARs, thereby facilitating induction of long-term potentiation by short bursts of high-frequency stimulation. Specific EAAT3 inhibitors may have the potential to locally and specifically strengthen particular synapses.

Obsessive-compulsive disorder (OCD) is among the most common mental disorders (prevalence 1-3%), and is at least as prevalent as schizophrenia and bipolar disorder. In the United States, one in 50 adults suffers from OCD. OCD affects children and adolescents as well as adults. Roughly one third to one half of adults with OCD reports a childhood onset of the disorder, and the disorder is typically chronic in nature. Treatment consists of predominantly serotonergic TCAs (clomipramine) or SSRIs in combination with cognitive-behavioral therapy (CBT). Overall, response to these interventions is of some but still limited benefit (approximately comparable to antidepressant response in MDD), and given the chronicity of OCD, the unmet medical need remains very high. OCD has been linked to serotonin and glutamate abnormalities. The hypothesis of glutamate signaling dysfunction in OCD is based on findings from neuroimaging, animal models, positional cloning and treatment studies.

The obsessive-compulsive symptomatology in OCD has considerable phenomenological, epidemiological and possibly (aetio)-pathophysiological overlap with a core autism spectrum disorder criterion: "restricted, repetitive patterns of behavior, interests, or activities" (taken from proposed DSM-5 revision). In support of this notion, human genetics studies have linked both the serotonin transporter and EAAT3 (SLC1A1) genes to autism spectrum disorder (ASD) or rigid-compulsive behavior in ASD and to OCD.

In addition, obsessive-compulsive symptoms induced by antipsychotics in schizophrenic bipolar disorder patients have been linked to EAAT3 (SLC1A1) gene variants. Post-mortem brain studies have shown that both classic and atypical antipsychotics reduce EAAT3, suggesting an involvement of this transporter in neuroleptic mechanisms beyond dopamine and serotonin modulation. Moreover, genetic variation in the human gene EAAT3 (SLC1A1) has been associated with antipsychotic drug response.

There is converging evidence from neurobiological data, human genetics, imaging studies and experimental treatments that EAAT3 is a key pathophysiological element in OCD and rigid-compulsive behavior in autism and in schizophrenia: A. A. Jensen et al., Curr. Opin. Pharmacol. 20, 116-123, 2015; L. A. Jarzylo abd H-Y. Man, J. Neurosci., 32, 2552-2563, 2012; A. Scimemi et al., J. Neurosci 29, 14581-14595, 2009; J. R. Wendland et al. Arch. Gen. Psychiatry, 66, 408-416, 2009; R. Bridges and C. S. Esslinger, Pharmacol. Ther. 107, 271-285, 2005; A. Nieoullon et al., J. Neurochem. 98, 1007-1018, 2006; K. Aoyama et al., Nat. Neurosci., 9, 119-126, 2006.

BRIEF SUMMARY OF THE INVENTION

The present invention relates to compounds of formula I wherein:

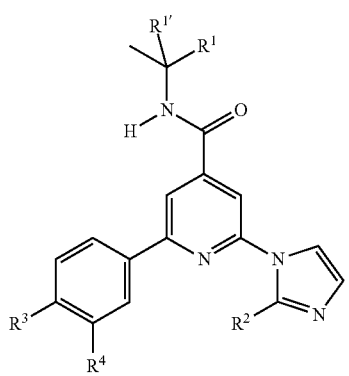

R[1'] is CH₃;
R[1] is methyl, ethyl, CF₃, CH₂OH, cyclopropyl or cyano, or R[1'] and R[1] may form together a 1,1-dioxo-tetrahydro-thiophen-3-yl ring;
R[2] is hydrogen, methyl, ethyl, isopropyl, tertbutyl, cyclopropyl, hydroxmethyl, or 2-propyl-2-ol;
R[3] is Cl, F, CF₃, methyl, methoxy, isopropyl, cyano or cyclopropyl;
R[4] is hydrogen, methyl, F or Cl;
or to a pharmaceutically acceptable salt or acid addition salt, to a racemic mixture, or to its corresponding enantiomer and/or optical isomer and/or stereoisomer thereof.

The compounds of formula I may be used in the treatment of psychiatric disorders such as schizophrenia, bipolar disorder, obsessive-compulsive disorder or autism spectrum disorder.

DETAILED DESCRIPTION OF THE INVENTION

It has been surprisingly been found that the compounds of general formula I are EAAT3 inhibitors.
Compounds of formula I are distinguished by having valuable therapeutic properties. They can be used in the treatment or prevention of disorders, relating to EAAT3 inhibitors.
The most preferred indications for compounds which are EAAT3 inhibitors are psychiatric disorders such as schizophrenia, bipolar disorder, obsessive-compulsive disorder or autism spectrum disorder.

The present invention relates to compounds of formula I and to their pharmaceutically acceptable salts, to their use in the treatment of psychiatric disorders such as schizophrenia, bipolar disorder, obsessive-compulsive disorder or autism spectrum disorder, to compounds of formulas I, IA, IB, IC, ID, IE, IF and IG as pharmaceutically active substances, to the processes for their production as well as to their use in the treatment or prevention of disorders, relating to EAAT3 inhibitors, such as schizophrenia, bipolar disorder, obsessive-compulsive disorder or autism spectrum disorder and to pharmaceutical compositions containing the compounds of formula IA A further object of the present invention is a method for the treatment or prophylaxis of psychiatric disorder such as schizophrenia, bipolar disorder, obsessive-compulsive disorder or autism spectrum disorder, which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

One object of the present invention are novel compounds of formula IA,

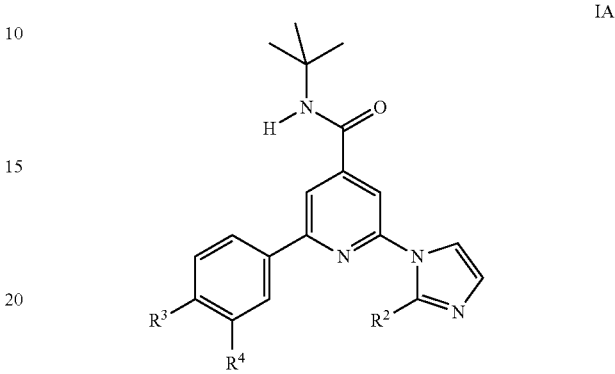

wherein
R[2] is hydrogen, methyl, ethyl, isopropyl, tertbutyl, cyclopropyl, hydroxmethyl, or 2-propyl-2-ol;
R[3] is Cl, F, CF₃, methyl, methoxy, isopropyl, cyano or cyclopropyl;
R[4] is hydrogen, methyl, F or Cl;
or a pharmaceutically acceptable salt or acid addition salt, a racemic mixture, or its corresponding enantiomer and/or optical isomer and/or stereoisomer thereof, for example the following compounds:

N-tert-Butyl-2-(4-chlorophenyl)-6-(2-propan-2-yl-imidazol-1-yl)-pyridine-4-carboxamide
N-tert-Butyl-2-(4-fluorophenyl)-6-(2-propan-2-yl-imidazol-1-yl)-pyridine-4-carboxamide
N-tert-Butyl-2-(2-propan-2-yl-imidazol-1-yl)-6-[4-(trifluoromethyl)-phenyl]-pyridine-4-carboxamide
N-tert-Butyl-2-(2-cyclopropyl-imidazol-1-yl)-6-(4-fluorophenyl)-pyridine-4-carboxamide
N-tert-Butyl-2-(4-chlorophenyl)-6-(2-cyclopropyl-imidazol-1-yl)-pyridine-4-carboxamide
N-tert-Butyl-2-(4-fluorophenyl)-6-imidazol-1-yl-pyridine-4-carboxamide
N-tert-Butyl-2-(4-fluorophenyl)-6-(2-methyl-imidazol-1-yl)-pyridine-4-carboxamide
N-tert-Butyl-2-(2-ethyl-imidazol-1-yl)-6-(4-fluorophenyl)-pyridine-4-carboxamide
N-tert-Butyl-2-(4-chlorophenyl)-6-imidazol-1-yl-pyridine-4-carboxamide
N-tert-Butyl-2-(4-chlorophenyl)-6-(2-methyl-imidazol-1-yl)-pyridine-4-carboxamide
N-tert-Butyl-2-(4-chlorophenyl)-6-(2-ethyl-imidazol-1-yl)-pyridine-4-carboxamide
N-tert-Butyl-2-(2-tert-butyl-imidazol-1-yl)-6-(4-chlorophenyl)-pyridine-4-carboxamide
N-tert-Butyl-2-(2-tert-butyl-imidazol-1-yl)-6-(4-fluorophenyl)-pyridine-4-carboxamide
N-tert-Butyl-2-(4-fluorophenyl)-6-[2-(hydroxymethyl)-imidazol-1-yl]-pyridine-4-carboxamide
N-tert-Butyl-2-(4-fluorophenyl)-6-[2-(2-hydroxypropan-2-yl)-imidazol-1-yl]-pyridine-4-carboxamide
N-tert-Butyl-2-(2-tert-butylimidazol-1-yl)-6-[4-(trifluoromethyl)-phenyl]-pyridine-4-carboxamide N-tert-Butyl-2-(2-cyclopropyl-imidazol-1-yl)-6-[4-(trifluoromethyl)-phenyl]-pyridine-4-carboxamide N-tert-Butyl-2-(2-methyl-imidazol-1-yl)-6-[4-(trifluoromethyl)-phenyl]-pyridine-4-carboxamide N-tert-Butyl-2-(4-chlorophenyl)-6-[2-(hydroxymethyl)-imidazol-1-yl]-pyridine-4-carboxamide N-tert-Butyl-2-(2-tert-butyl-imidazol-1-yl)-6-(3,4-difluorophenyl)-pyridine-4-carboxamide N-tert-Butyl-2-(2-tert-butyl-imidazol-1-yl)-6-(4-methylphenyl)-pyridine-4-carboxamide N-tert-Butyl-2-(2-tert-butyl-imidazol-1-yl)-6-(4-cyclopropyl-phenyl)-pyridine-4-carboxamide N-tert-Butyl-2-(2-tert-butyl-imidazol-1-yl)-6-(4-fluoro-3-methyl-phenyl)-pyridine-4-carboxamide N-tert-Butyl-2-(2-tert-butyl-imidazol-1-yl)-6-(4-methoxyphenyl)-pyridine-4-carboxamide N-tert-Butyl-2-(2-tert-butyl-imidazol-1-yl)-6-(4-cyano-phenyl)-pyridine-4-carboxamide N-tert-Butyl-2-(4-chlorophenyl)-6-[2-(2-hydroxypropan-2-yl)-imidazol-1-yl]-pyridine-4-carboxamide or N-tert-Butyl-2-[2-(2-hydroxypropan-2-yl)-imidazol-1-yl]-6-[4-(trifluoromethyl)-phenyl]-pyridine-4-carboxamide.

One further object of the present invention are novel compounds of formula IB,

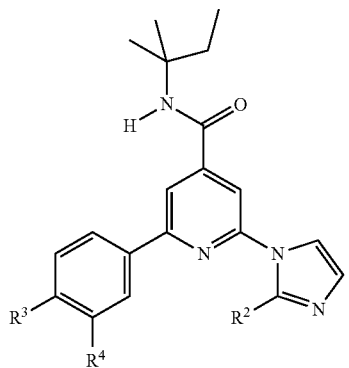

IB wherein
$R^2$ is hydrogen, methyl, ethyl, isopropyl, tertbutyl, cyclopropyl, hydroxmethyl, or 2-propyl-2-ol;
$R^3$ is Cl, F, $CF_3$, methyl, methoxy, isopropyl, cyano or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the compound 2-(4-Fluorophenyl)-N-(2-methylbutan-2-yl)-6-(2-propan-2-ylimidazol-1-yl)-pyridine-4-carboxamide.

One object of the present invention are novel compounds of formula IC,

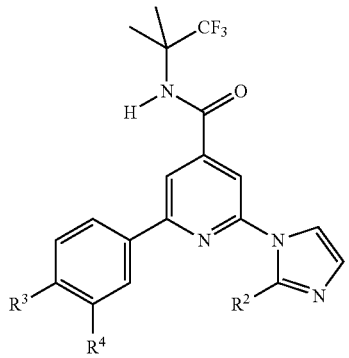

IC wherein
$R^2$ is hydrogen, methyl, ethyl, isopropyl, tertbutyl, cyclopropyl, hydroxmethyl, or 2-propyl-2-ol;
$R^3$ is Cl, F, $CF_3$, methyl, methoxy, isopropyl, cyano or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the compounds
2-(4-Chlorophenyl)-6-(2-propan-2-yl-imidazol-1-yl)-N-(1,1,1-trifluoro-2-methylpropan-2-yl)-pyridine-4-carboxamide
2-(4-Chlorophenyl)-6-(2-cyclopropyl-imidazol-1-yl)-N-(1,1,1-trifluoro-2-methylpropan-2-yl)-pyridine-4-carboxamide
2-(2-tert-Butylimidazol-1-yl)-6-(4-chlorophenyl)-N-(1,1,1-trifluoro-2-methylpropan-2-yl)-pyridine-4-carboxamide
2-(4-Chlorophenyl)-6-[2-(2-hydroxypropan-2-yl)-imidazol-1-yl]-N-(1,1,1-trifluoro-2-methylpropan-2-yl)-pyridine-4-carboxamide.

One object of the present invention are novel compounds of formula ID,

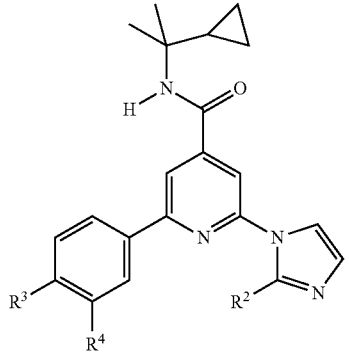

ID wherein
$R^2$ is hydrogen, methyl, ethyl, isopropyl, tertbutyl, cyclopropyl, hydroxmethyl, or 2-propyl-2-ol;
$R^3$ is Cl, F, $CF_3$, methyl, methoxy, isopropyl, cyano or cyclopropyl;
$R^4$ is hydrogen, methyl, F or Cl;
or a pharmaceutically acceptable salt or acid addition salt, a racemic mixture, or its corresponding enantiomer and/or optical isomer and/or stereoisomer thereof, for example the compounds 2-(4-Chlorophenyl)-N-(2-cyclopropylpropan-2-yl)-6-(2-propan-2-yl-imidazol-1-yl)-pyridine-4-carboxamide
2-(4-Chlorophenyl)-6-(2-cyclopropyl-imidazol-1-yl)-N-(2-cyclopropyl-propan-2-yl)-pyridine-4-carboxamide
2-(2-tert-Butylimidazol-1-yl)-6-(4-chlorophenyl)-N-(2-cyclopropyl-propan-2-yl)-pyridine-4-carboxamide or
2-(4-Chlorophenyl)-N-(2-cyclopropylpropan-2-yl)-6-[2-(2-hydroxypropan-2-yl)-imidazol-1-yl]-pyridine-4-carboxamide.

One further object of the invention are compounds of formula IE,

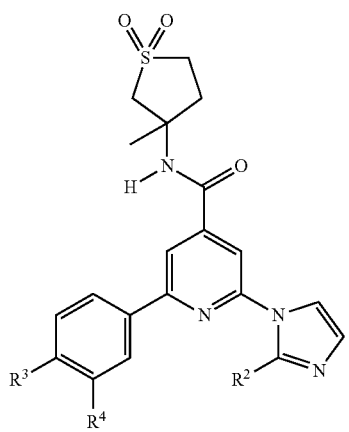

IE wherein
R² is hydrogen, methyl, ethyl, isopropyl, tertbutyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt, a racemic mixture, or its corresponding enantiomer and/or optical isomer and/or stereoisomer thereof, for example the compound (RS)-2-(4-Fluorophenyl)-N-(3-methyl-1,1-dioxothiolan-3-yl)-6-(2-propan-2-ylimidazol-1-yl)-pyridine-4-carboxamide.

One further object of the invention are compounds of formula IF,

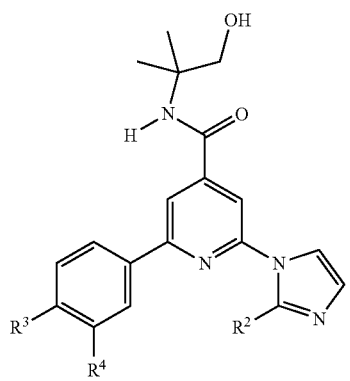

IF wherein
R² is hydrogen, methyl, ethyl, isopropyl, tertbutyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt, a racemic mixture, or its corresponding enantiomer and/or optical isomer and/or stereoisomer thereof, for example the compound 2-(4-Chlorophenyl)-N-(1-hydroxy-2-methylpropan-2-yl)-6-(2-propan-2-yl-imidazol-1-yl)-pyridine-4-carboxamide.

One further object of the invention are compounds of formula IG,

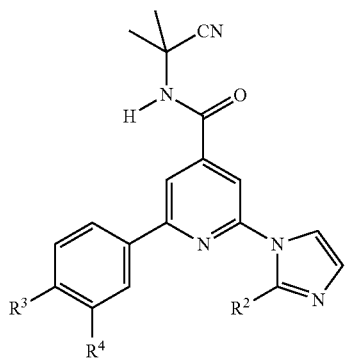

IG wherein
R² is hydrogen, methyl, ethyl, isopropyl, tertbutyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt, a racemic mixture, or its corresponding enantiomer and/or optical isomer and/or stereoisomer thereof, for example the compounds
2-(2-tert-Butylimidazol-1-yl)-6-(4-chlorophenyl)-N-(2-cyanopropan-2-yl)-pyridine-4-carboxamide or
2-(4-Chlorophenyl)-N-(2-cyanopropan-2-yl)-6-(2-propan-2-yl-imidazol-1-yl)-pyridine-4-carboxamide.

The preparation of compounds of formulas IA, IB, IC, ID, IE, IF and IG of the present invention may be carried out in sequential or convergent synthetic routes. Syntheses of the compounds of the invention are shown in the following schemes 1 to 5. The skills required for carrying out the reaction and purification of the resulting products are known to those skilled in the art. The substituents and indices used in the following description of the processes have the significance given herein before.

The compounds of formulas IA, IB, IC, ID, IE, IF and IG can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of IA, IB, IC, ID, IE, IF and IG and their pharmaceutically acceptable salts may be prepared by methods, known in the art, for example by the process variant described below, which process comprises a) reacting a compound of formula

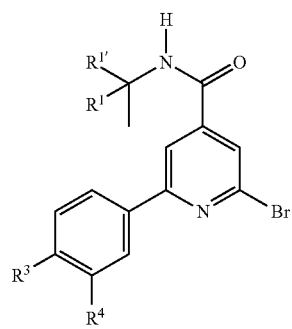

II with a compound of formula

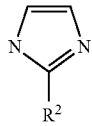

III to a compound of formula I

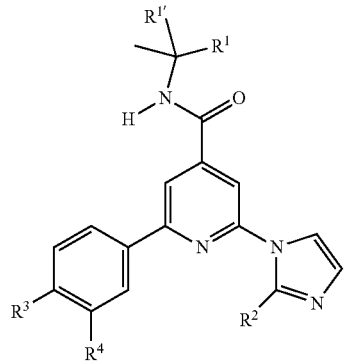

I wherein the substituents are as described above, or
if desired, converting the compounds obtained into pharmaceutically acceptable acid addition salts.

b) reacting a compound of formula

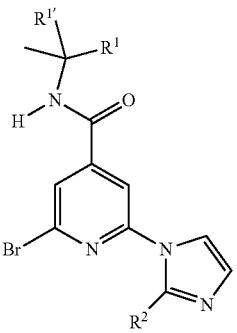

IV with a compound of formula

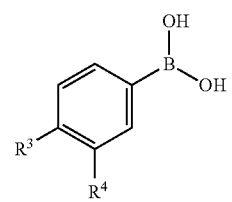

V to a compound of formula I

I wherein the substituents are described above, or
if desired, converting the compounds obtained into pharmaceutically acceptable acid addition salts.

The preparation of compounds of formulas IA, IB, IC, ID, IE, IF and IG is further described in more detail in scheme 1 to 5 and in examples 1-40.

The imidazole derivatives I can either be prepared from the intermediate bromo derivatives II by substitution reaction with commercially available imidazoles III

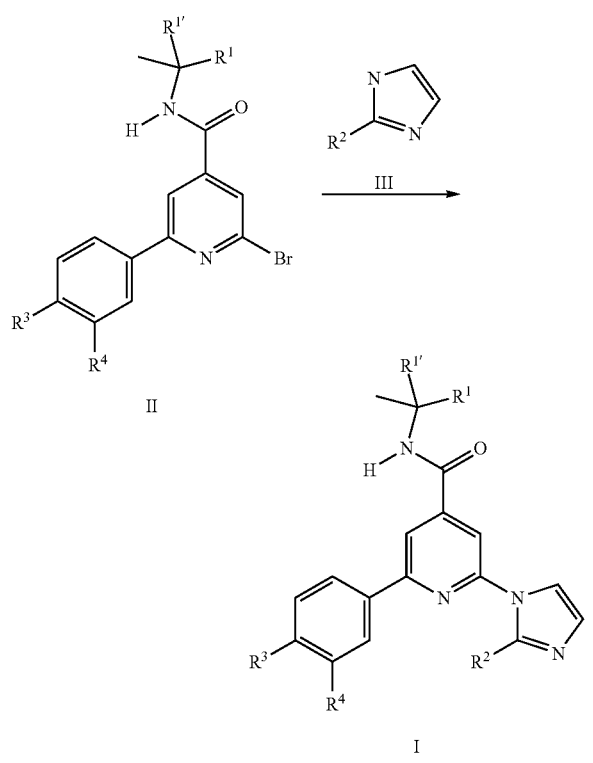

or by coupling reaction of the bromo derivatives IV with commercially available boronic acid derivatives V.

The bromo derivatives II can be prepared starting from commercially available 2,6-dibromo-isonicotinic acid VI. Amide formation with the commercially available amines VII using standard conditions leads to the amides VIII which can be coupled with commercially available boronic acid derivatives V to yield the final building blocks II.

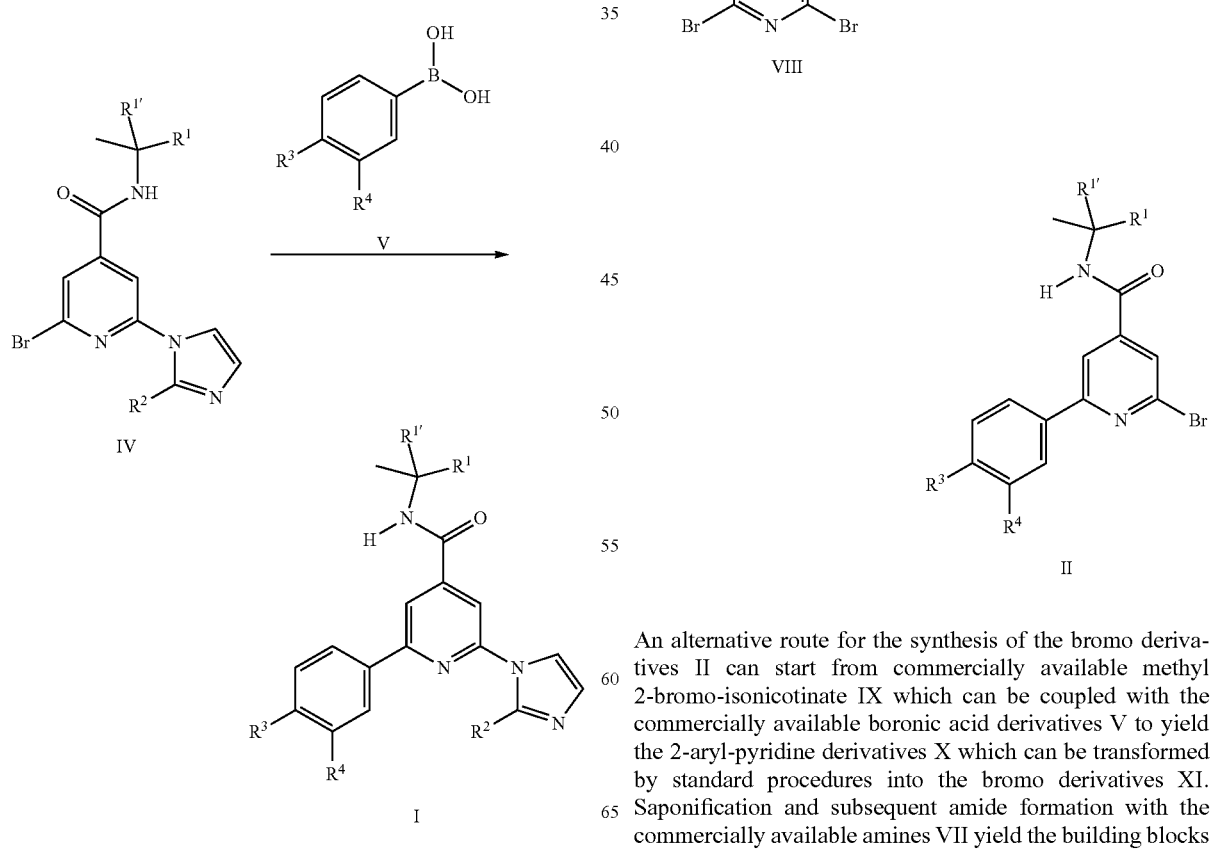

An alternative route for the synthesis of the bromo derivatives II can start from commercially available methyl 2-bromo-isonicotinate IX which can be coupled with the commercially available boronic acid derivatives V to yield the 2-aryl-pyridine derivatives X which can be transformed by standard procedures into the bromo derivatives XI. Saponification and subsequent amide formation with the commercially available amines VII yield the building blocks II.

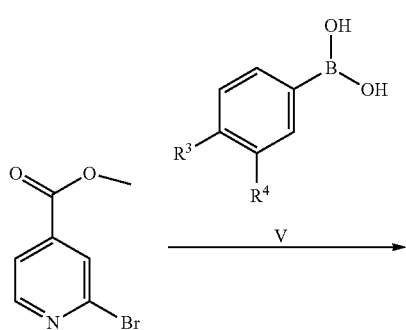
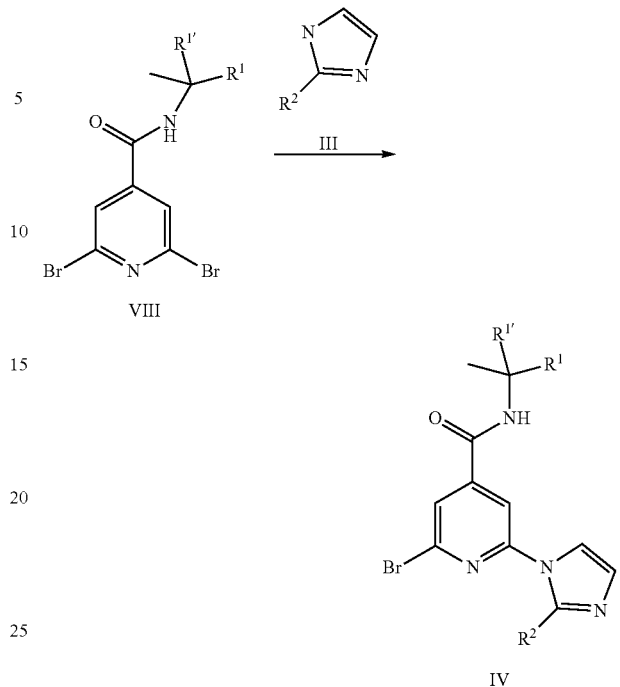
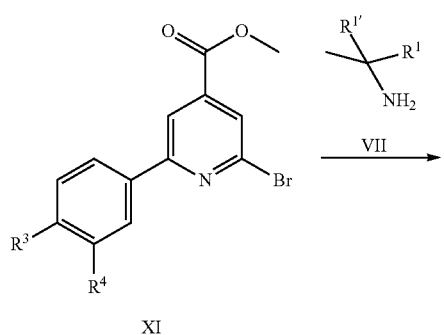
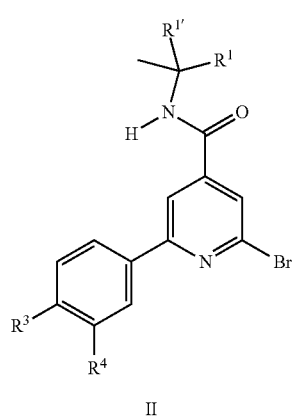

The synthesis of the bromo derivatives IV can be performed starting from the above described amides VIII which can be reacted with the commercially available imidazoles III to yield after reverse phase HPLC separation of the obtained product mixture the pure building blocks IV.

Generally speaking, the sequence of steps used to synthesize the compounds of formula I can also be modified in certain cases.

The compounds of formula I and their pharmaceutically usable addition salts possess valuable pharmaceutical properties. Specifically, it has been found that the compounds of the present invention are EAAT3 inhibitors for use in the treatment of schizophrenia, bipolar disorder, obsessive-compulsive disorder or autism spectrum disorders.

The compounds were investigated in accordance with the test given hereinafter.

Biological Assay and Data

The FLIPR Membrane Potential (FMP) Assay

HEK-293 cells stably expressing human EAAT3 were seeded at 55 000 cells/well in growth medium (DMEM glutamate free (Invitrogen 11960-044), 1% Pen Strep (10 ml/l GIBCO BRL No 15140-023), 10% FCS non dialysed heat inactivated, 5 mg/l puromycin) in poly-D-lysine treated 96-well black microtiter plates with clear-bottom. After 24 h, the growth medium was removed and 100 μl/well of Krebs buffer (140 mM NaCl, 4.7 mM KCl, 2.5 mM $CaCl_2$, 1.2 mM $MgCl_2$, 11 mM HEPES, 10 mM D-glucose, pH=7.4) added. The cells were then loaded by adding 100 μl/well FMP assay dye (FLIPR Membrane Potential assay reagent, Molecular Devices). The 96-well plates were then incubated at 37° C. for 1 h. The depolarization of the cells will cause more dye to enter in the cells, where it will bind to intracellular proteins and lipids and cause an increase in the fluorescence signal. Antagonist potency at human EAAT3 was determined by using L-glutamate as agonist at a concentration which gives 80% of the maximum response. The antagonists were applied 15 min before the application of the agonist L-glutamate. The assays were performed at room temperature and measurements done by using a Fluorometric Imaging Plate Reader (FLIPR, Molecular Devices)

and filter #2. Responses were measured as peak increase in fluorescence minus basal (i.e. fluorescence without addition of L-glutamate). Kb was determined using the Cheng-Prusoff equation $Kb=IC_{50}/[1+(A/EC_{50})]$, where $IC_{50}$ is the concentration of the antagonist producing 50% inhibition, A is the concentration of the agonist against which the $IC_{50}$ is being determined (at $EC_{80}$) and $EC_{50}$ is the concentration of the agonist producing 50% inhibition.

LIST OF EXAMPLES AND DATA

| | Structure | Compound name | EAAT3 Kb [uM] |
|---|---|---|---|
| 1 | 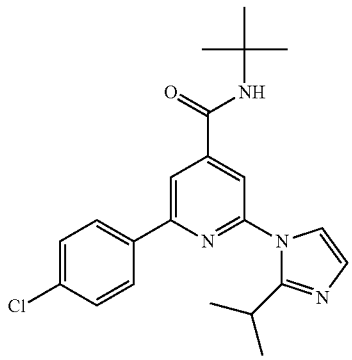 [SMILES: CC(C)c1nccn1-c1cc(C(=O)NC(C)(C)C)cc(-c2ccc(Cl)cc2)n1] | N-tert-Butyl-2-(4-chlorophenyl)-6-(2-propan-2-yl-imidazol-1-yl)-pyridine-4-carboxamide | 0.14 |
| 2 | 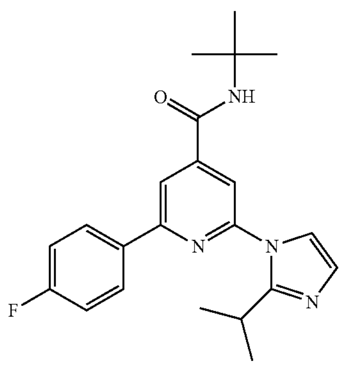 [SMILES: CC(C)c1nccn1-c1cc(C(=O)NC(C)(C)C)cc(-c2ccc(F)cc2)n1] | N-tert-Butyl-2-(4-fluorophenyl)-6-(2-propan-2-yl-imidazol-1-yl)-pyridine-4-carboxamide | 0.11 |
| 3 | 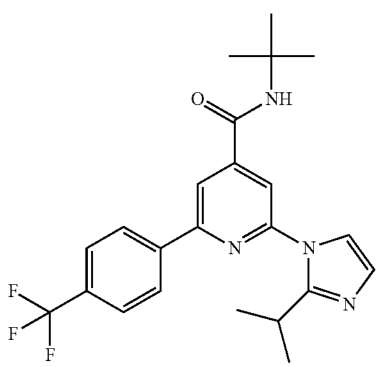 [SMILES: CC(C)c1nccn1-c1cc(C(=O)NC(C)(C)C)cc(-c2ccc(C(F)(F)F)cc2)n1] | N-tert-Butyl-2-(2-propan-2-yl-imidazol-1-yl)-6-[4-(trifluoromethyl)-phenyl]-pyridine-4-carboxamide | 0.46 |
| 4 | 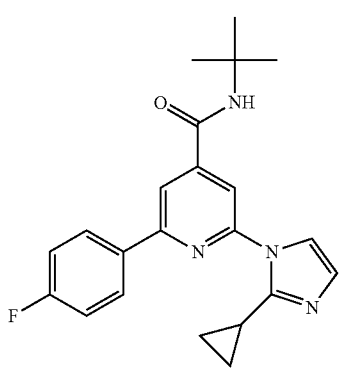 [SMILES: CC(C)(C)NC(=O)c1cc(-c2ccc(F)cc2)nc(-n2ccnc2C2CC2)c1] | N-tert-Butyl-2-(2-cyclopropyl-imidazol-1-yl)-6-(4-fluorophenyl)-pyridine-4-carboxamide | 0.16 |

-continued
| | Structure | Compound name | EAAT3 Kb [uM] |
|---|---|---|---|
| 5 | 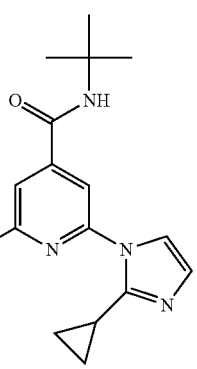 | N-tert-Butyl-2-(4-chlorophenyl)-6-(2-cyclopropyl-imidazol-1-yl)-pyridine-4-carboxamide | 0.12 |
| 6 | 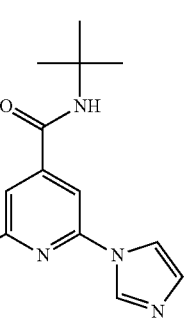 | N-tert-Butyl-2-(4-fluorophenyl)-6-imidazol-1-yl-pyridine-4-carboxamide | 1.0 |
| 7 | 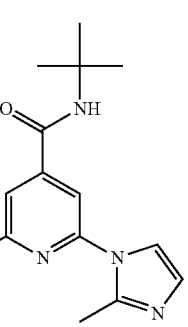 | N-tert-Butyl-2-(4-fluorophenyl)-6-(2-methyl-imidazol-1-yl)-pyridine-4-carboxamide | 0.43 |
| 8 | 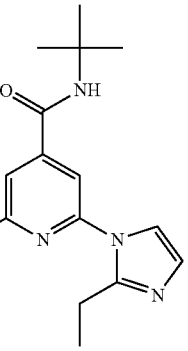 | N-tert-Butyl-2-(2-ethyl-imidazol-1-yl)-6-(4-fluorophenyl)-pyridine-4-carboxamide | 0.21 |

-continued

| Structure | Compound name | EAAT3 Kb [uM] |
|---|---|---|
| 9 | N-tert-Butyl-2-(4-chlorophenyl)-6-imidazol-1-yl-pyridine-4-carboxamide | 0.6 |
| 10 | N-tert-Butyl-2-(4-chlorophenyl)-6-(2-methyl-imidazol-1-yl)-pyridine-4-carboxamide | 0.3 |
| 11 | N-tert-Butyl-2-(4-chlorophenyl)-6-(2-ethyl-imidazol-1-yl)-pyridine-4-carboxamide | 0.25 |
| 12 | N-tert-Butyl-2-(2-tert-butyl-imidazol-1-yl)-6-(4-chlorophenyl)-pyridine-4-carboxamide | 0.063 |

-continued

| | | EAAT3 Kb |
|---|---|---|
| Structure | Compound name | [uM] |

13 N-tert-Butyl-2-(2-tert-butyl-imidazol-1-yl)-6-(4-fluorophenyl)-pyridine-4-carboxamide  0.058

14 N-tert-Butyl-2-(4-fluorophenyl)-6-[2-(hydroxymethyl)-imidazol-1-yl]-pyridine-4-carboxamide  0.37

15 2-(4-Chlorophenyl)-N-(2-cyclopropylpropan-2-yl)-6-(2-propan-2-yl-imidazol-1-yl)-pyridine-4-carboxamide  0.15

16 2-(4-Chlorophenyl)-6-(2-cyclopropyl-imidazol-1-yl)-N-(2-cyclopropyl-propan-2-yl)-pyridine-4-carboxamide  0.3

| Structure | Compound name | EAAT3 Kb [uM] |
|---|---|---|
| 17 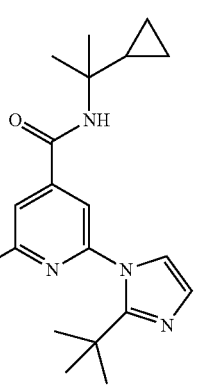 | 2-(2-tert-Butylimidazol-1-yl)-6-(4-chlorophenyl)-N-(2-cyclopropyl-propan-2-yl)-pyridine-4-carboxamide | 0.28 |
| 18 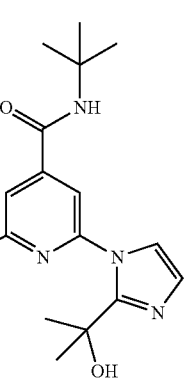 | N-tert-Butyl-2-(4-fluorophenyl)-6-[2-(2-hydroxypropan-2-yl)-imidazol-1-yl]-pyridine-4-carboxamide | 0.1 |
| 19 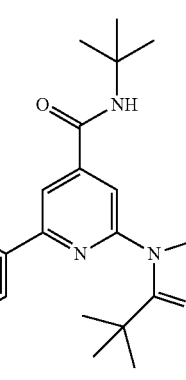 | N-tert-Butyl-2-(2-tert-butylimidazol-1-yl)-6-[4-(trifluoromethyl)-phenyl]-pyridine-4-carboxamide | 0.18 |
| 20 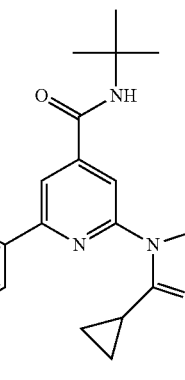 | N-tert-Butyl-2-(2-cyclopropyl-imidazol-1-yl)-6-[4-(trifluoromethyl)-phenyl]-pyridine-4-carboxamide | 0.29 |

-continued

| | Structure | Compound name | EAAT3 Kb [uM] |
|---|---|---|---|
| 21 | 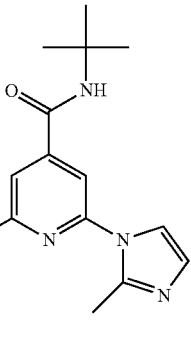 | N-tert-Butyl-2-(2-methyl-imidazol-1-yl)-6-[4-(trifluoromethyl)-phenyl]-pyridine-4-carboxamide | 0.65 |
| 22 | 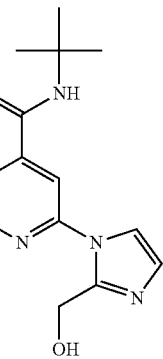 | N-tert-Butyl-2-(4-chlorophenyl)-6-[2-(hydroxymethyl)-imidazol-1-yl]-pyridine-4-carboxamide | 0.5 |
| 23 | 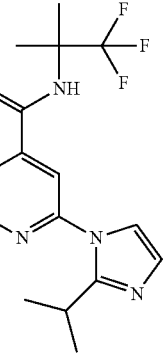 | 2-(4-Chlorophenyl)-6-(2-propan-2-yl-imidazol-1-yl)-N-(1,1,1-trifluoro-2-methylpropan-2-yl)-pyridine-4-carboxamide | 0.32 |
| 24 | 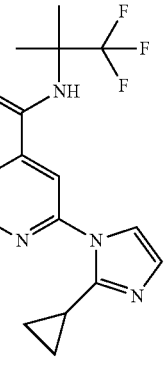 | 2-(4-Chlorophenyl)-6-(2-cyclopropyl-imidazol-1-yl)-N-(1,1,1-trifluoro-2-methylpropan-2-yl)-pyridine-4-carboxamide | 0.51 |

| | Structure | Compound name | EAAT3 Kb [uM] |
|---|---|---|---|
| 25 | 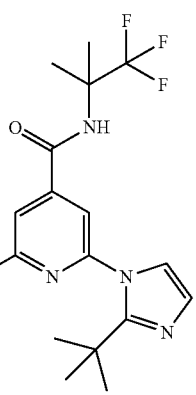 | 2-(2-tert-Butylimidazol-1-yl)-6-(4-chlorophenyl)-N-(1,1,1-trifluoro-2-methylpropan-2-yl)-pyridine-4-carboxamide | 0.26 |
| 26 | 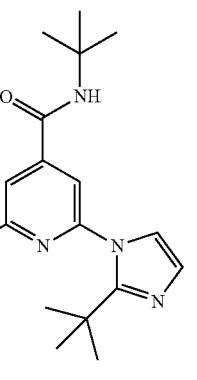 | N-tert-Butyl-2-(2-tert-butyl-imidazol-1-yl)-6-(3,4-difluorophenyl)-pyridine-4-carboxamide | 0.37 |
| 27 | 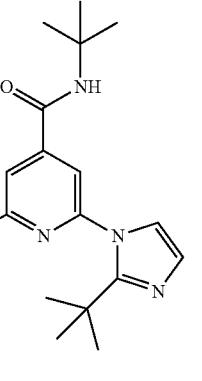 | N-tert-Butyl-2-(2-tert-butyl-imidazol-1-yl)-6-(4-methylphenyl)-pyridine-4-carboxamide | 0.11 |
| 28 | 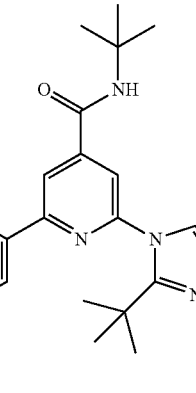 | N-tert-Butyl-2-(2-tert-butyl-imidazol-1-yl)-6-(4-cyclopropyl-phenyl)-pyridine-4-carboxamide | 0.67 |

-continued
| Structure | Compound name | EAAT3 Kb [uM] |
|---|---|---|
| 29 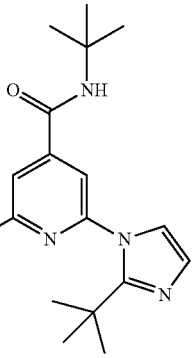 | N-tert-Butyl-2-(2-tert-butyl-imidazol-1-yl)-6-(4-fluoro-3-methyl-phenyl)-pyridine-4-carboxamide | 0.15 |
| 30 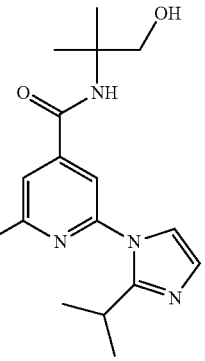 | 2-(4-Chlorophenyl)-N-(1-hydroxy-2-methylpropan-2-yl)-6-(2-propan-2-yl-imidazol-1-yl)-pyridine-4-carboxamide | 0.19 |
| 31 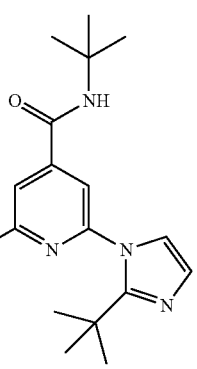 | N-tert-Butyl-2-(2-tert-butyl-imidazol-1-yl)-6-(4-methoxy-phenyl)-pyridine-4-carboxamide | 0.24 |
| 32 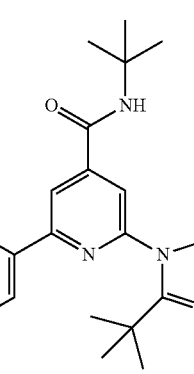 | N-tert-Butyl-2-(2-tert-butyl-imidazol-1-yl)-6-(4-cyano-phenyl)-pyridine-4-carboxamide | 0.29 |

-continued

| Structure | Compound name | EAAT3 Kb [uM] |
|---|---|---|
| 33 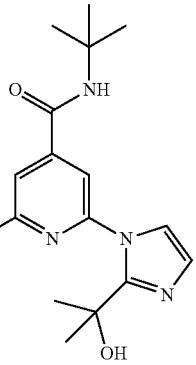 | N-tert-Butyl-2-(4-chlorophenyl)-6-[2-(2-hydroxypropan-2-yl)-imidazol-1-yl]-pyridine-4-carboxamide | 0.17 |
| 34 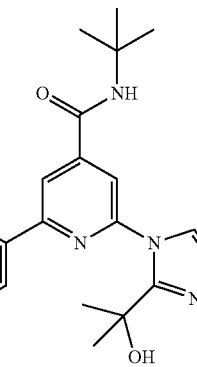 | N-tert-Butyl-2-[2-(2-hydroxypropan-2-yl)-imidazol-1-yl]-6-[4-(trifluoromethyl)-phenyl]-pyridine-4-carboxamide | 0.24 |
| 35 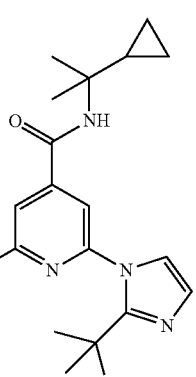 | 2-(4-Chlorophenyl)-N-(2-cyclopropylpropan-2-yl)-6-[2-(2-hydroxypropan-2-yl)-imidazol-1-yl]-pyridine-4-carboxamide | 0.15 |
| 36 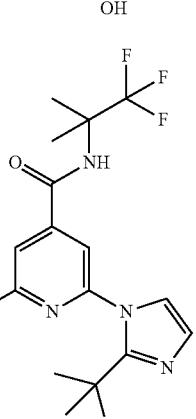 | 2-(4-Chlorophenyl)-6-[2-(2-hydroxypropan-2-yl)-imidazol-1-yl]-N-(1,1,1-trifluoro-2-methylpropan-2-yl)-pyridine-4-carboxamide | 0.078 |

-continued

| Structure | Compound name | EAAT3 Kb [uM] |
|---|---|---|
| 37 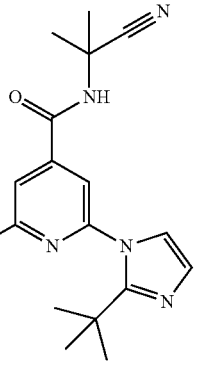 | 2-(2-tert-Butylimidazol-1-yl)-6-(4-chlorophenyl)-N-(2-cyanopropan-2-yl)-pyridine-4-carboxamide | 0.096 |
| 38 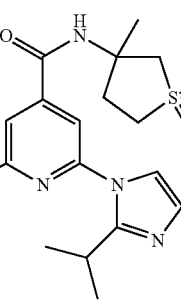 | (RS)-2-(4-Fluorophenyl)-N-(3-methyl-1,1-dioxothiolan-3-yl)-6-(2-propan-2-ylimidazol-1-yl)-pyridine-4-carboxamide | 0.14 |
| 39 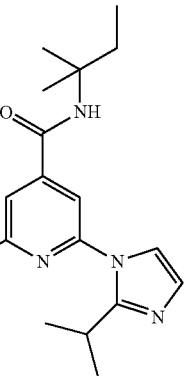 | 2-(4-Fluorophenyl)-N-(2-methylbutan-2-yl)-6-(2-propan-2-ylimidazol-1-yl)-pyridine-4-carboxamide | 0.069 |
| 40 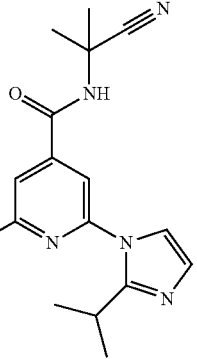 | 2-(4-Chlorophenyl)-N-(2-cyanopropan-2-yl)-6-(2-propan-2-yl-imidazol-1-yl)-pyridine-4-carboxamide | 0.36 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Experimental Section

Intermediates

Intermediate 1: 2-Bromo-N-tert-butyl-6-(4-fluorophenyl)-pyridine-4-carboxamide

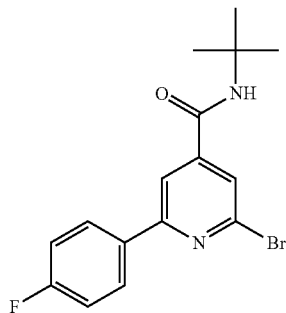 [SMILES: CC(C)(C)NC(=O)c1cc(Br)nc(-c2ccc(F)cc2)c1]

Step A

To a stirred solution of commercially available 2,6-dibromoisonicotinic acid (3 g, 10.7 mmol) in THF (77 ml) was added N,N-diisopropylethylamine (3.45 g, 4.66 ml, 26.7 mmol), commercially available 2-methylpropan-2-amine (956 mg, 1.37 ml, 12.8 mmol) and TBTU (4.46 g, 13.9 mmol). The reaction mixture was allowed to stir for 17 h at room temperature, filtered, evaporated and purified by flash chromatography on silica gel [heptane/ethyl acetate (0-50%)] to yield 2,6-dibromo-N-tert-butylpyridine-4-carboxamide (3.28 g, 91%) as an off-white solid, MS (ISP) m/z=337.0 [(M+H)+], mp 148° C.

Step B

A mixture of 2,6-dibromo-N-tert-butylpyridine-4-carboxamide (3.28 g, 9.76 mmol), commercially available (4-fluorophenyl)-boronic acid (1.37 g, 9.76 mmol), potassium carbonate (1.35 g, 9.76 mmol) and PdCl$_2$(dppf) (239 mg, 293 μmol) in methanol (39 ml) was heated at 100° C. for 10 min in a microwave reactor. The reaction mixture was filtered and purified by flash chromatography on silica gel [heptane/ethyl acetate 4:1] to give 3.32 g of an off-white solid which was further purified by reverse phase HPLC (acetonitrile/formic acid 98:2) to yield the title compound (1.59 g, 46%) as an off-white solid, MS (ISP) m/z=351.1 [(M+H)+], mp 209° C.

Intermediate 2: 2-Bromo-N-tert-butyl-6-(4-chlorophenyl)-pyridine-4-carboxamide

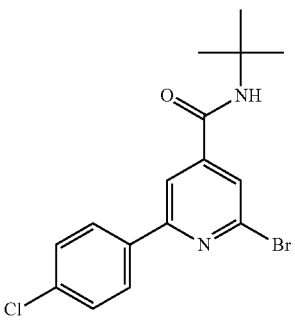 [SMILES: CC(C)(C)NC(=O)c1cc(Br)nc(-c2ccc(Cl)cc2)c1]

The title compound, white solid (0.74 g, 31%), MS (ISP) m/z=369.0 [(M+H)+], mp 208° C., was prepared in accordance with the general method of intermediate 1, step B, from 2,6-dibromo-N-tert-butylpyridine-4-carboxamide (intermediate 1, step A) (2.18 g, 6.49 mmol) and commercially available (4-chlorophenyl)-boronic acid (1.01 g, 6.49 mmol).

Intermediate 3: 2-Bromo-N-tert-butyl-6-[4-(trifluoromethyl)-phenyl]-pyridine-4-carboxamide

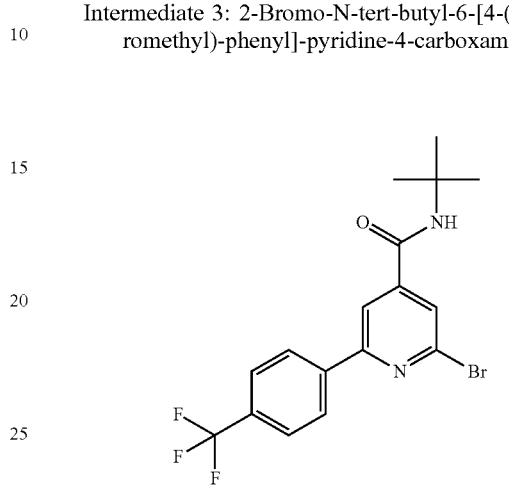

The title compound, white solid (1.02 g, 40%), MS (ISP) m/z=403.0 [(M+H)+], mp 239° C., was prepared in accordance with the general method of intermediate 1, step B, from 2,6-dibromo-N-tert-butylpyridine-4-carboxamide (intermediate 1, step A) (2.15 g, 6.40 mmol) and commercially available (4-trifluoromethylphenyl)-boronic acid (1.22 g, 6.40 mmol).

Intermediate 4: 2-Bromo-6-(4-chlorophenyl)-N-(2-cyclopropylpropan-2-yl)-pyridine-4-carboxamide

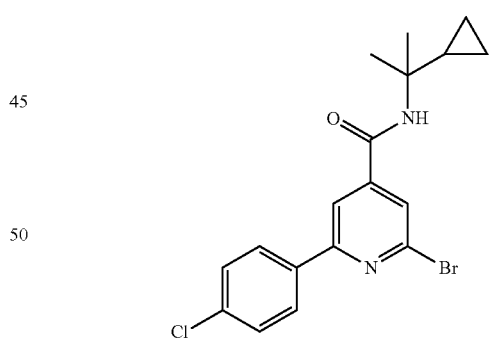

Step A 2,6-Dibromo-N-(2-cyclopropylpropan-2-yl)-pyridine-4-carboxamide, white solid (2.48 g, 96%), MS (ISP) m/z=363.0 [(M+H)+], mp 119° C., was prepared in accordance with the general method of intermediate 1, step A, from commercially available 2,6-dibromo-isonicotinic acid (2.0 g, 7.12 mmol) and commercially available 2-cyclopropylpropan-2-amine hydrochloride (1.16 g, 8.54 mmol).

Step B

The title compound, white solid (0.70 g, 26%), MS (ISP) m/z=395.0 [(M+H)+], mp 185° C., was prepared in accordance with the general method of intermediate 1, step B, from 2,6-dibromo-N-(2-cyclopropylpropan-2-yl)-pyridine-4-carboxamide (intermediate 4, step A) (2.48 g, 6.85 mmol) and commercially available (4-chlorophenyl)-boronic acid (1.07 g, 6.85 mmol).

Intermediate 5: 2-Bromo-6-(4-chlorophenyl)-N-(1,1,1-trifluoro-2-methylpropan-2-yl)-pyridine-4-carboxamide

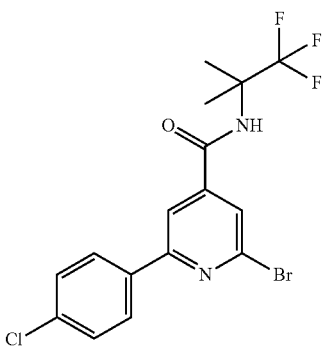 [SMILES: CC(C)(NC(=O)c1cc(Br)nc(-c2ccc(Cl)cc2)c1)C(F)(F)F]

Step A

A mixture of commercially available methyl 2-bromoisonicotinate (3.0 g, 13.9 mmol), commercially available (4-chlorophenyl)-boronic acid (2.61 g, 16.7 mmol), potassium carbonate (2.30 g, 16.7 mmol) and PdCl$_2$(dppf) (340 mg, 417 µmol) in methanol (27 ml) was heated at 100° C. for 10 min in a microwave reactor. The reaction mixture was filtered and purified by flash chromatography on silica gel [heptane/ethyl acetate 4:1] to yield methyl 2-(4-chlorophenyl)-pyridine-4-carboxylate (3.16 g, 92%) as a white solid, MS (ISP) m/z=248.1 [(M+H)$^+$], mp 74° C.

Step B

A stirred solution of methyl 2-(4-chlorophenyl)-pyridine-4-carboxylate (3.15 g, 12.7 mmol) in dichloromethane (36 ml) was cooled to 0° C. in an ice-bath, m-chloro-perbenzoic acid (5.7 g, 25.4 mmol) was added and the reaction mixture was allowed to stir for 17 h at room temperature. 1N NaOH (60 ml) was added and the mixture was extracted with dichloromethane (2×50 ml). The combined organic layers were washed with saturated sodium bicarbonate solution (50 ml) and brine (50 ml), dried (MgSO$_4$) and evaporated to yield methyl 2-(4-chlorophenyl)-1-oxido-1-pyridinium-4-carboxylate (3.15 g, 94%) as an off-white solid, MS (ISP) m/z=264.0 [(M+H)$^+$], mp 135° C.

Step C

A stirred solution of methyl 2-(4-chlorophenyl)-1-oxido-1-pyridinium-4-carboxylate (3.15 g, 11.9 mmol) in toluene (60 ml) was heated to 80° C., phosphorus oxybromide (13.7 g, 47.8 mmol) was added and the reaction mixture was allowed to stir for 2 h at 80° C. The reaction mixture was cooled to room temperature, poured into ice/water (100 ml) and extracted with ethyl acetate (2×70 ml). The combined organic layers were washed with brine (70 ml), dried (MgSO$_4$) and evaporated. The crude product (4.25 g) was further purified by flash chromatography on silica gel (DCM/MeOH 95:5) to yield methyl 2-bromo-6-(4-chlorophenyl)-pyridine-4-carboxylate (1.40 g, 36%) as an off-white solid, MS (ISP) m/z=327.9 [(M+H)$^+$], mp 101° C.

Step D

To a stirred solution of methyl 2-bromo-6-(4-chlorophenyl)-pyridine-4-carboxylate (1.40 g, 4.29 mmol) in THF (7 ml), methanol (7 ml) and water (7 ml), lithium hydroxide monohydrate (234 mg, 5.57 mmol) was added and the reaction mixture was allowed to stir for 3 h at room temperature. The reaction mixture was concentrated to one third, 2N HCl solution (5 ml) was added, the precipitate was collected by filtration, washed with water and dried to yield 2-bromo-6-(4-chlorophenyl)-pyridine-4-carboxylic acid (1.18 g, 88%) as a white solid, MS (ISP) m/z=313.9 [(M+H)$^+$], mp 191° C.

Step E

A stirred solution of 2-bromo-6-(4-chlorophenyl)-pyridine-4-carboxylic acid (500 mg, 1.6 mmol) in THF (12.8 ml) was cooled in an ice bath to 0° C., oxalyl chloride (4.63 g, 3.19 ml, 36.5 mmol) and DMF (64.2 µl) were added, the reaction mixture was allowed to stir for 1 h at room temperature, and evaporated. THF (13 ml), 1,1,1-trifluoro-2-methylpropan-2-amine (244 mg, 220 µl, 1.92 mmol) and N,N-diisopropylethylamine (724 mg, 958 µl, 5.6 mmol) were added, the reaction mixture was allowed to stir for 17 h at room temperature and evaporated. Purification by flash chromatography on silica gel [heptane/ethyl acetate (0-50%)] yielded the title compound (0.58 g, 86%) as an off-white solid, MS (ISN) m/z=421.2 [(M−H)], mp 192° C.

Intermediate 6: 2-Bromo-6-(4-chlorophenyl)-N-(2-cyanopropan-2-yl)-pyridine-4-carboxamide

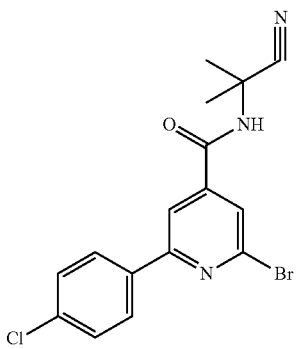 [SMILES: CC(C)(C#N)NC(=O)c1cc(Br)nc(-c2ccc(Cl)cc2)c1]

The title compound, light brown foam (352 mg, 93%), MS (ISP) m/z=380.0 [(M+H)$^+$], was prepared in accordance with the general method of intermediate 5, step E, from 2-bromo-6-(4-chlorophenyl)-pyridine-4-carboxylic acid (intermediate 5, step D) (313 mg, 1.0 mmol) and commercially available 2-amino-2-methylpropanenitrile (126 mg, 1.5 mmol).

Intermediate 7: 2-Bromo-6-(4-chlorophenyl)-N-(1-hydroxy-2-methylpropan-2-yl)-pyridine-4-carboxamide

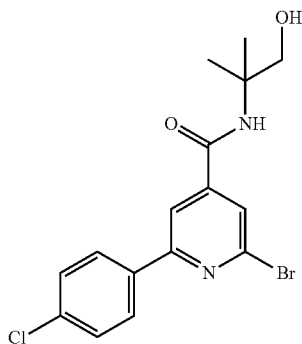 [SMILES: CC(C)(CO)NC(=O)c1cc(Br)nc(-c2ccc(Cl)cc2)c1]

To a stirred solution of 2-bromo-6-(4-chlorophenyl)-pyridine-4-carboxylic acid (intermediate 5, step D) (313 mg, 1.0 mmol) in THF (7.2 ml) was added at room temperature N,N-diisopropylethylamine (323 mg, 437 µl, 2.5 mmol), commercially available 2-amino-2-methylpropan-1-ol (134 mg, 144 µl, 1.5 mmol) and TBTU (514 mg, 1.6 mmol). The reaction mixture was allowed to stir for 17 h at room temperature, filtered and purified by flash chromatography [heptane/ethyl acetate (20-80%)] to yield title compound (284 mg, 74%) as a white solid, MS (ISN) m/z=385.0 [(M+H)$^+$], mp 174° C.

Intermediate 8: 2-Bromo-N-tert-butyl-6-(3,4-difluorophenyl)-pyridine-4-carboxamide

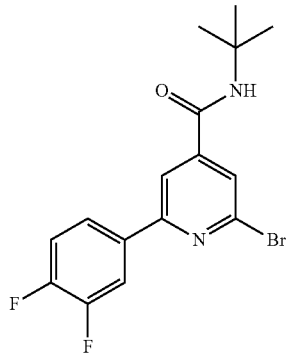

The title compound, light brown solid (139 mg, 36%), MS (ISP) m/z=371.0 [(M+H)$^+$], mp 219° C., was prepared in accordance with the general method of intermediate 1, step B, from 2,6-dibromo-N-tert-butylpyridine-4-carboxamide (intermediate 1, step A) (350 mg, 1.04 mmol) and commercially available (3,4-difluorophenyl)-boronic acid (164 mg, 1.04 mmol).

Intermediate 9: 2-Bromo-N-tert-butyl-6-(4-chloro-3-fluorophenyl)-pyridine-4-carboxamide

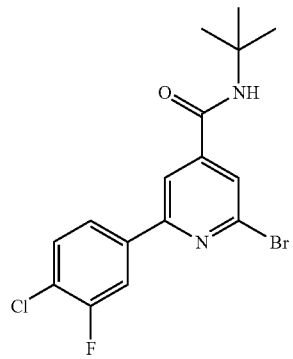 [SMILES: CC(C)(C)NC(=O)c1cc(Br)nc(-c2ccc(F)c(F)c2)c1]

The title compound, light brown solid (123 mg, 31%), MS (ISP) m/z=387.0 [(M+H)$^+$], mp 220° C., was prepared in accordance with the general method of intermediate 1, step B, from 2,6-dibromo-N-tert-butylpyridine-4-carboxamide (intermediate 1, step A) (350 mg, 1.04 mmol) and commercially available (4-chloro-3-fluorophenyl)-boronic acid (182 mg, 1.04 mmol).

Intermediate 10: 2-Bromo-N-tert-butyl-6-(3-fluoro-4-methylphenyl)-pyridine-4-carboxamide

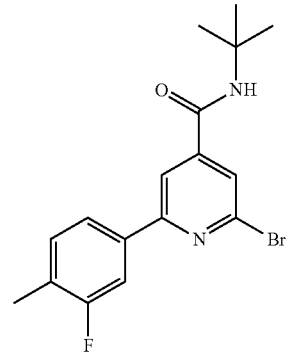 [SMILES: Cc1ccc(-c2cc(C(=O)NC(C)(C)C)cc(Br)n2)cc1F]

The title compound, off-white solid (134 mg, %), MS (ISP) m/z=367.1 [(M+H)$^+$], mp 194° C., was prepared in accordance with the general method of intermediate 1, step B, from 2,6-dibromo-N-tert-butylpyridine-4-carboxamide (intermediate 1, step A) (350 mg, 1.04 mmol) and commercially available (3-fluoro-4-methylphenyl)-boronic acid (160 mg, 1.04 mmol).

Intermediate 11: 2-Bromo-N-tert-butyl-6-(4-methyl-phenyl)-pyridine-4-carboxamide

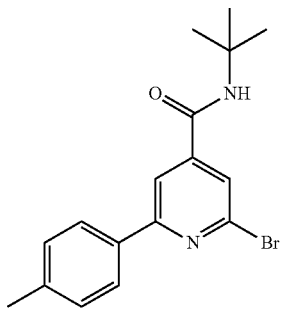 [SMILES: Cc1ccc(-c2cc(C(=O)NC(C)(C)C)cc(Br)n2)cc1]

The title compound, white solid (147 mg, 41%), MS (ISP) m/z=349.1 [(M+H)$^+$], mp 179° C., was prepared in accordance with the general method of intermediate 1, step B, from 2,6-dibromo-N-tert-butylpyridine-4-carboxamide (intermediate 1, step A) (350 mg, 1.04 mmol) and commercially available (4-methylphenyl)-boronic acid (142 mg, 1.04 mmol).

Intermediate 12: 2-Bromo-N-tert-butyl-6-(4-cyclo-propylphenyl)-pyridine-4-carboxamide

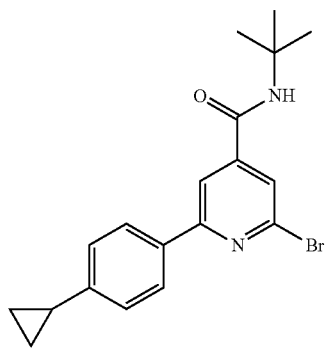 [SMILES: CC(C)(C)NC(=O)c1cc(Br)nc(-c2ccc(C3CC3)cc2)c1]

The title compound, white solid (160 mg, 41%), MS (ISP) m/z=375.1 [(M+H)$^+$], mp 202° C., was prepared in accordance with the general method of intermediate 1, step B, from 2,6-dibromo-N-tert-butylpyridine-4-carboxamide (intermediate 1, step A) (350 mg, 1.04 mmol) and commercially available (4-cyclopropylphenyl)-boronic acid (169 mg, 1.04 mmol).

Intermediate 13: 2-Bromo-N-tert-butyl-6-(4-fluoro-3-methylphenyl)-pyridine-4-carboxamide

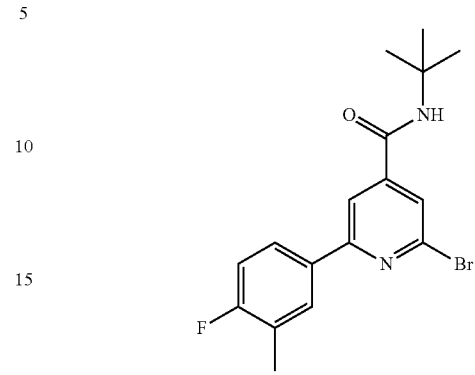

The title compound, white solid (152 mg, 40%), MS (ISP) m/z=365.1 [(M+H)$^+$], mp 192° C., was prepared in accordance with the general method of intermediate 1, step B, from 2,6-dibromo-N-tert-butylpyridine-4-carboxamide (intermediate 1, step A) (350 mg, 1.04 mmol) and commercially available (4-fluoro-3-methylphenyl)-boronic acid (160 mg, 1.04 mmol).

Intermediate 14: 2-Bromo-N-tert-butyl-6-(2-tert-butylimidazol-1-yl)-pyridine-4-carboxamide

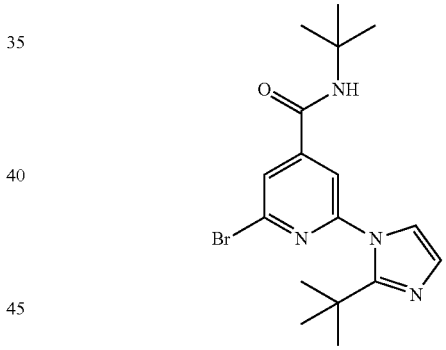

A microwave tube was charged with 2,6-dibromo-N-tert-butylpyridine-4-carboxamide (intermediate 1, step A) (0.84 g, 2.5 mmol), 2-(tert-butyl)-1H-imidazole (310 mg, 2.5 mmol), potassium phosphate (1.06 g, 5 mmol) and tetrabutylammoniumbromide (403 mg, 1.25 mmol), DMSO (5 ml) was added, the reaction mixture purged with argon for 5 min in an ultrasonic bath, copper(I)iodide (47.6 mg, 250 µmol) and 4,7-dihydroxy-1,10-phenanthroline (106 mg, 500 µmol) were added, the tube was sealed and the reaction mixture was allowed to stir for 20 h at 120° C. The reaction mixture was cooled to room temperature, diluted with water (10 ml), and the precipitate collected by filtration. The crude product (950 mg) was purified by flash chromatography on silica gel [heptane/ethyl acetate (20-80%)] to yield the title compound (494 mg, 52%) as an off-white solid, MS (ISN) m/z=381.1 [(M+H)$^+$], mp 216° C.

Intermediate 15: N-tert-Butyl-2-(4-chlorophenyl)-6-iodopyridine-4-carboxamide

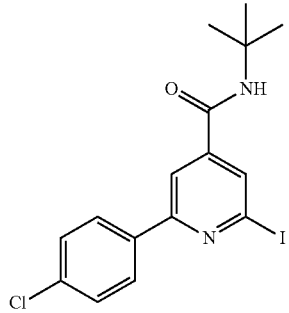 [SMILES: CC(C)(C)NC(=O)c1cc(I)nc(-c2ccc(Cl)cc2)c1]

A mixture of 2-bromo-N-tert-butyl-6-(4-chlorophenyl)-pyridine-4-carboxamide (intermediate 2) (304 mg, 827 μmol), sodium iodide (372 mg, 2.48 mmol), copper(I)iodide (7.87 mg, 41.3 μmol) and N,N'-dimethylenediamine (7.29 mg, 8.9 μl, 82.7 μmol) in 1,4-dioxane (2 ml) was allowed to stir for 2 h at 110° C., poured into a cold mixture of NH$_4$OH solution (30 ml) and extracted with ethyl acetate (2×40 ml). The combined organic layers were washed with brine (50 ml), dried (MgSO$_4$) and evaporated. The crude product (390 mg, light yellow foam) was purified by flash chromatography on silica gel (heptane/ethyl acetate 4:1) to yield the title compound (328 mg, 96%) as a white solid, MS (ISN) m/z=415.0 [(M+H)$^+$], mp 177° C.

Intermediate 16: N-tert-Butyl-2-iodo-6-[4-(trifluoromethyl)-phenyl]-pyridine-4-carboxamide

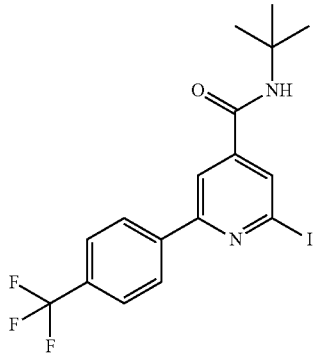 [SMILES: CC(C)(C)NC(=O)c1cc(I)nc(-c2ccc(C(F)(F)F)cc2)c1]

The title compound, white solid (517 mg, 94%), MS (ISP) m/z=449.1 [(M+H)$^+$], mp 213° C., was prepared in accordance with the general method of intermediate 15 from 2-bromo-N-tert-butyl-6-[4-(trifluoromethyl)-phenyl]-pyridine-4-carboxamide (intermediate 3) (495 mg, 1.23 mmol).

Intermediate 17: 2-(4-Chlorophenyl)-N-(2-cyclopropylpropan-2-yl)-6-iodopyridine-4-carboxamide

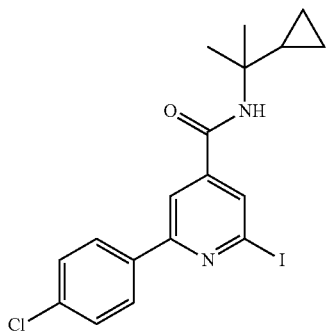 [SMILES: CC(C)(NC(=O)c1cc(I)nc(-c2ccc(Cl)cc2)c1)C1CC1]

The title compound, white solid (195 mg, 97%), MS (ISP) m/z=441.1 [(M+H)$^+$], mp 157° C., was prepared in accordance with the general method of intermediate 15 from 2-bromo-6-(4-chlorophenyl)-N-(2-cyclopropylpropan-2-yl)-pyridine-4-carboxamide (intermediate 4) (180 mg, 0.46 mmol).

Intermediate 18: 2-(4-Chlorophenyl)-6-iodo-N-(1,1,1-trifluoro-2-methylpropan-2-yl)-pyridine-4-carboxamide

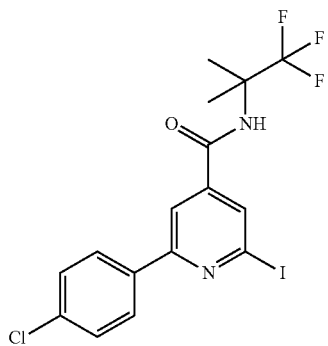 [SMILES: CC(C)(NC(=O)c1cc(I)nc(-c2ccc(Cl)cc2)c1)C(F)(F)F]

The title compound, off-white solid (153 mg, 94%), MS (ISP) m/z=469.1 [(M+H)$^+$], mp 179° C., was prepared in accordance with the general method of intermediate 15 from 2-bromo-6-(4-chlorophenyl)-N-(1,1,1-trifluoro-2-methylpropan-2-yl)-pyridine-4-carboxamide (intermediate 5) (147 mg, 0.35 mmol).

Intermediate 19: 2-(4-Chlorophenyl)-N-(2-cyano-propan-2-yl)-6-iodopyridine-4-carboxamide

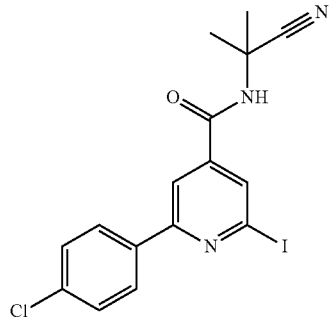 [SMILES: CC(C)(C#N)NC(=O)c1cc(I)nc(-c2ccc(Cl)cc2)c1]

The title compound, white foam (380 mg, 89%), MS (ISP) m/z=426.0 [(M+H)⁺], was prepared in accordance with the general method of intermediate 15 from 2-bromo-6-(4-chlorophenyl)-N-(2-cyanopropan-2-yl)-pyridine-4-carboxamide (intermediate 6) (380 mg, 1.0 mmol).

Intermediate 20: (RS)-2-Bromo-6-(4-fluorophenyl)-N-(3-methyl-1,1-dioxothiolan-3-yl)-pyridine-4-carboxamide

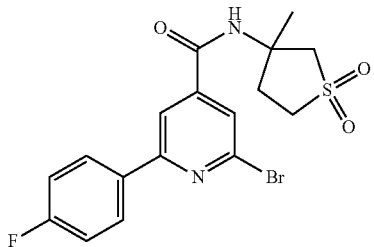 [SMILES: CC1(NC(=O)c2cc(Br)nc(-c3ccc(F)cc3)c2)CCS(=O)(=O)C1]

Step A (RS)-2,6-Dibromo-N-(3-methyl-1,1-dioxothiolan-3-yl)-pyridine-4-carboxamide, white foam (0.97 g, 94%), MS (ISP) m/z=413.0 [(M+H)⁺], was prepared in accordance with the general method of intermediate 1, step A, from commercially available 2,6-dibromo-isonicotinic acid (0.70 g, 2.50 mmol) and commercially available (RS)-3-amino-3-methyltetrahydro-thiophene 1,1-dioxide hydrochloride (0.56 g, 3.0 mmol).

Step B

The title compound, white foam (498 mg, 50%), MS (ISP) m/z=429.0 [(M+H)⁺], was prepared in accordance with the general method of intermediate 1, step B, from (RS)-2,6-dibromo-N-(3-methyl-1,1-dioxothiolan-3-yl)-pyridine-4-carboxamide (0.96 g, 2.33 mmol) and commercially available (4-fluorophenyl)-boronic acid (326 mg, 2.33 mmol).

Intermediate 21: 2-Bromo-6-(4-fluorophenyl)-N-(2-methylbutan-2-yl)-pyridine-4-carboxamide

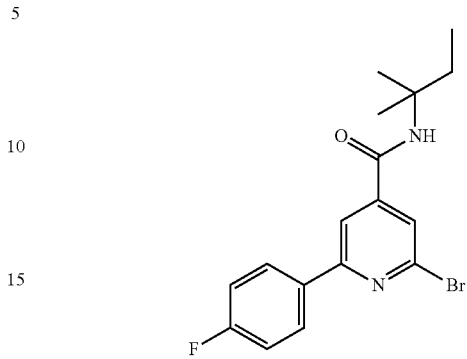

Step A 2,6-Dibromo-N-(2-methylbutan-2-yl)-pyridine-4-carboxamide, light brown solid (0.79 g, 90%), MS (ISP) m/z=351.0 [(M+H)⁺], mp 92° C., was prepared in accordance with the general method of intermediate 1, step A, from commercially available 2,6-dibromo-isonicotinic acid (0.70 g, 2.50 mmol) and commercially available 2-methylbutan-2-amine (0.26 g, 3.0 mmol).

Step B

The title compound, white solid (303 mg, 37%), MS (ISP) m/z=367.1 [(M+H)⁺], mp 193° C., was prepared in accordance with the general method of intermediate 1, step B, from 2,6-dibromo-N-(2-methylbutan-2-yl)-pyridine-4-carboxamide (0.78 g, 2.23 mmol) and commercially available (4-fluorophenyl)-boronic acid (312 mg, 2.23 mmol).

Example 1

N-tert-Butyl-2-(4-chlorophenyl)-6-(2-propan-2-yl-imidazol-1-yl)-pyridine-4-carboxamide

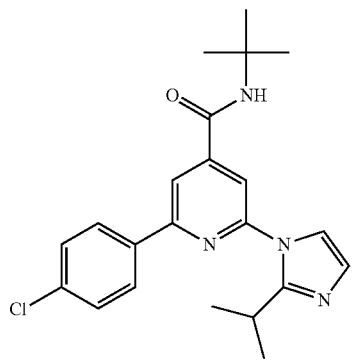 [SMILES: CC(C)c1nccn1-c1cc(C(=O)NC(C)(C)C)cc(-c2ccc(Cl)cc2)n1]

A mixture of 2-bromo-N-tert-butyl-6-(4-chlorophenyl)-pyridine-4-carboxamide (intermediate 2) (91.9 mg, 250 µmol), commercially available 2-isopropyl-1H-imidazole (55.1 mg, 500 µmol) and potassium carbonate (69.1 mg, 500 µmol) in DMSO (1.5 ml) was purged with argon in an ultrasonic bath for 5 min, N,N-dimethylglycine (10.3 mg, 100 µmol) and copper(I)iodide (9.52 mg, 50 µmol) were added, the tube sealed and heated for 17 h at 115° C. The reaction mixture was diluted with water (10 ml), the precipitate collected by filtration and further purified by flash chromatography on silica gel [heptane/ethyl acetate (50-100%)] to yield the title compound (50 mg, 50%) as an off-white foam, MS (ISN) m/z=397.3 [(M+H)+].

Example 2

N-tert-Butyl-2-(4-fluorophenyl)-6-(2-propan-2-yl-imidazol-1-yl)-pyridine-4-carboxamide

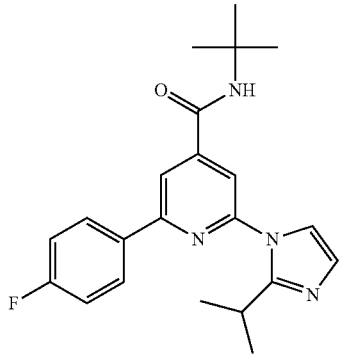

The title compound, off-white solid (55 mg, 58%), MS (ISP) m/z=381.3 [(M+H)+], mp 199° C., was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 2-isopropyl-1H-imidazole (55.1 mg, 500 μmol).

Example 3

N-tert-Butyl-2-(2-propan-2-yl-imidazol-1-yl)-6-[4-(trifluoromethyl)-phenyl]-pyridine-4-carboxamide

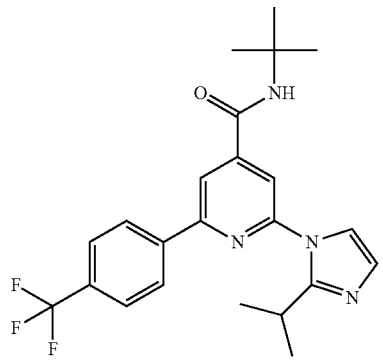 [SMILES: CC(C)c1nccn1-c1cc(C(=O)NC(C)(C)C)cc(-c2ccc(C(F)(F)F)cc2)n1]

The title compound, white foam (68 mg, 63%), MS (ISP) m/z=431.3 [(M+H)+], was prepared in accordance with the general method of example 1 from 2-bromo-N-tert-butyl-6-[4-(trifluoromethyl)-phenyl]-pyridine-4-carboxamide (intermediate 3) (100 mg, 0.25 mmol) and commercially available 2-isopropyl-1H-imidazole (55.1 mg, 500 μmol).

Example 4

N-tert-Butyl-2-(2-cyclopropyl-imidazol-1-yl)-6-(4-fluorophenyl)-pyridine-4-carboxamide

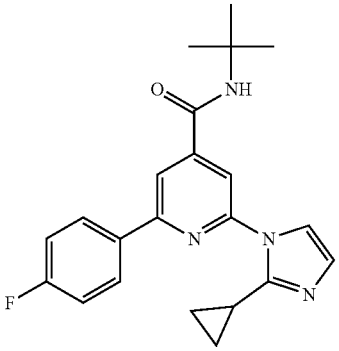 [SMILES: CC(C)(C)NC(=O)c1cc(-c2ccc(F)cc2)nc(-n2ccnc2C2CC2)c1]

The title compound, light yellow foam (66 mg, 70%), MS (ISP) m/z=379.2 [(M+H)+], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 2-cyclopropyl-1H-imidazole (54.1 mg, 500 μmol).

Example 5

N-tert-Butyl-2-(4-chlorophenyl)-6-(2-cyclopropyl-imidazol-1-yl)-pyridine-4-carboxamide

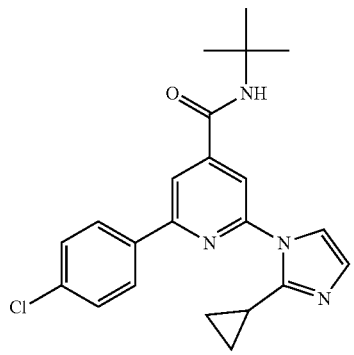 [SMILES: CC(C)(C)NC(=O)c1cc(-c2ccc(Cl)cc2)nc(-n2ccnc2C2CC2)c1]

The title compound, white foam (44 mg, 45%), MS (ISP) m/z=395.2 [(M+H)+], was prepared in accordance with the general method of example 1 from 2-bromo-N-tert-butyl-6-(4-chlorophenyl)-pyridine-4-carboxamide (intermediate 2) (91.9 mg, 250 μmol) and commercially available 2-cyclopropyl-1H-imidazole (54.1 mg, 500 μmol).

Example 6

N-tert-Butyl-2-(4-fluorophenyl)-6-imidazol-1-yl-pyridine-4-carboxamide

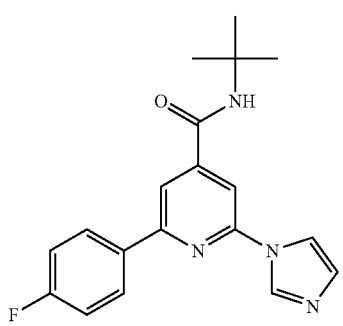 [SMILES: CC(C)(C)NC(=O)c1cc(-c2ccc(F)cc2)nc(-n2ccnc2)c1]

The title compound, off-white foam (81 mg, 96%), MS (ISP) m/z=339.2 [(M+H)$^+$], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 1H-imidazole (34.0 mg, 500 µmol).

Example 7

N-tert-Butyl-2-(4-fluorophenyl)-6-(2-methyl-imidazol-1-yl)-pyridine-4-carboxamide

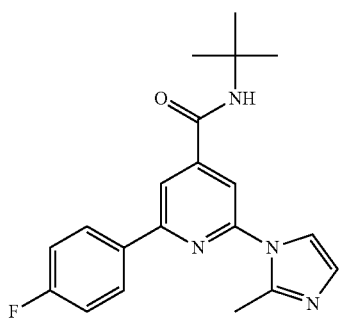 [SMILES: Cc1nccn1-c1cc(C(=O)NC(C)(C)C)cc(-c2ccc(F)cc2)n1]

The title compound, white foam (75 mg, 85%), MS (ISP) m/z=353.3 [(M+H)$^+$], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 2-methyl-1H-imidazole (41.1 mg, 500 µmol).

Example 8

N-tert-Butyl-2-(2-ethyl-imidazol-1-yl)-6-(4-fluorophenyl)-pyridine-4-carboxamide

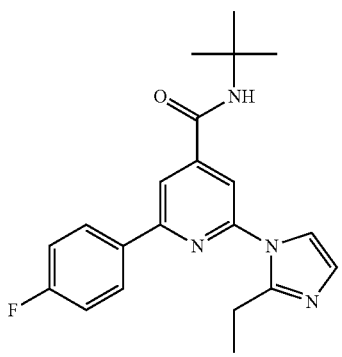 [SMILES: CCc1nccn1-c1cc(C(=O)NC(C)(C)C)cc(-c2ccc(F)cc2)n1]

The title compound, white foam (80 mg, 87%), MS (ISP) m/z=367.2 [(M+H)$^+$], was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available 2-ethyl-1H-imidazole (48.1 mg, 500 µmol).

Example 9

N-tert-Butyl-2-(4-chlorophenyl)-6-imidazol-1-yl-pyridine-4-carboxamide

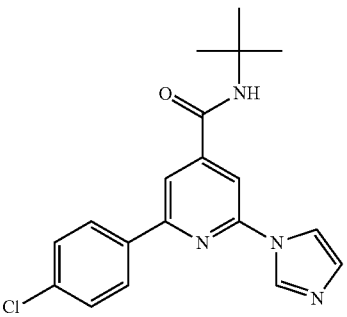 [SMILES: CC(C)(C)NC(=O)c1cc(-c2ccc(Cl)cc2)nc(-n2ccnc2)c1]

The title compound, white foam (85 mg, 96%), MS (ISP) m/z=355.1 [(M+H)$^+$], was prepared in accordance with the general method of example 1 from 2-bromo-N-tert-butyl-6-(4-chlorophenyl)-pyridine-4-carboxamide (intermediate 2) (91.9 mg, 250 µmol) and commercially available 1H-imidazole (34.0 mg, 500 µmol).

Example 10

N-tert-Butyl-2-(4-chlorophenyl)-6-(2-methyl-imidazol-1-yl)-pyridine-4-carboxamide

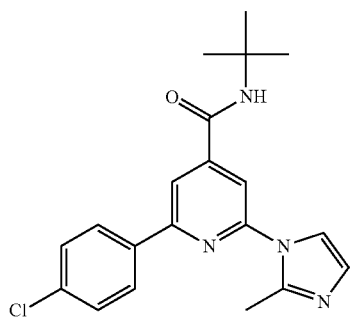 [SMILES: Cc1nccn1-c1cc(C(=O)NC(C)(C)C)cc(-c2ccc(Cl)cc2)n1]

The title compound, white foam (81 mg, 88%), MS (ISP) m/z=369.2 [(M+H)$^+$], was prepared in accordance with the general method of example 1 from 2-bromo-N-tert-butyl-6-(4-chlorophenyl)-pyridine-4-carboxamide (intermediate 2) (91.9 mg, 250 µmol) and commercially available 2-methyl-1H-imidazole (41.1 mg, 500 µmol).

Example 11

N-tert-Butyl-2-(4-chlorophenyl)-6-(2-ethyl-imidazol-1-yl)-pyridine-4-carboxamide

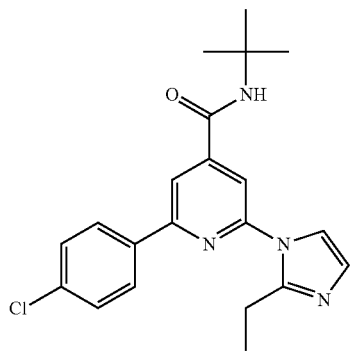 [SMILES: CCc1nccn1-c1cc(C(=O)NC(C)(C)C)cc(-c2ccc(Cl)cc2)n1]

The title compound, white solid (84 mg, 88%), MS (ISP) m/z=383.2 [(M+H)$^+$], was prepared in accordance with the general method of example 1 from 2-bromo-N-tert-butyl-6-(4-chlorophenyl)-pyridine-4-carboxamide (intermediate 2) (91.9 mg, 250 µmol) and commercially available 2-ethyl-1H-imidazole (48.1 mg, 500 µmol).

Example 12

N-tert-Butyl-2-(2-tert-butyl-imidazol-1-yl)-6-(4-chlorophenyl)-pyridine-4-carboxamide

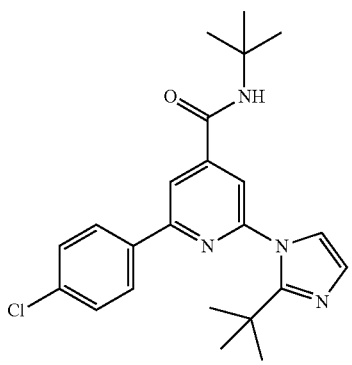 [SMILES: CC(C)(C)NC(=O)c1cc(-c2ccc(Cl)cc2)nc(-n2ccnc2C(C)(C)C)c1]

The title compound, light brown foam (31 mg, 30%), MS (ISP) m/z=411.2 [(M+H)$^+$], was prepared in accordance with the general method of intermediate 14 from 2-bromo-N-tert-butyl-6-(4-chlorophenyl)-pyridine-4-carboxamide (intermediate 2) (91.9 mg, 250 µmol) and commercially available 2-tert-butyl-1H-imidazole (37.3 mg, 300 µmol).

Example 13

N-tert-Butyl-2-(2-tert-butyl-imidazol-1-yl)-6-(4-fluorophenyl)-pyridine-4-carboxamide

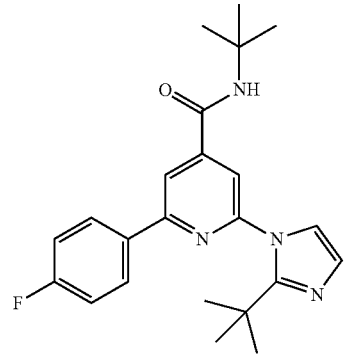 [SMILES: CC(C)(C)NC(=O)c1cc(-c2ccc(F)cc2)nc(-n2ccnc2C(C)(C)C)c1]

The title compound, off-white foam (22 mg, 22%), MS (ISP) m/z=395.3 [(M+H)$^+$], was prepared in accordance with the general method of intermediate 14 from 2-bromo-N-tert-butyl-6-(4-fluorophenyl)-pyridine-4-carboxamide (intermediate 1) (87.8 mg, 0.25 mmol) and commercially available 2-tert-butyl-1H-imidazole (37.3 mg, 300 µmol).

Example 14

N-tert-Butyl-2-(4-fluorophenyl)-6-[2-(hydroxymethyl)-imidazol-1-yl]-pyridine-4-carboxamide

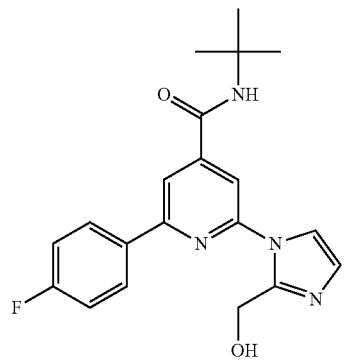 [SMILES: CC(C)(C)NC(=O)c1cc(-c2ccc(F)cc2)nc(-n2ccnc2CO)c1]

The title compound, off-white solid (48 mg, 52%), MS (ISP) m/z=369.2 [(M+H)⁺], mp 212° C., was prepared in accordance with the general method of example 1 from 2-bromo-N-tert-butyl-6-(4-fluorophenyl)-pyridine-4-carboxamide (intermediate 1) (87.8 mg, 0.25 mmol) and commercially available (1H-imidazol-2-yl)-methanol (49.1 mg, 500 μmol).

Example 15

2-(4-Chlorophenyl)-N-(2-cyclopropylpropan-2-yl)-6-(2-propan-2-yl-imidazol-1-yl)-pyridine-4-carboxamide

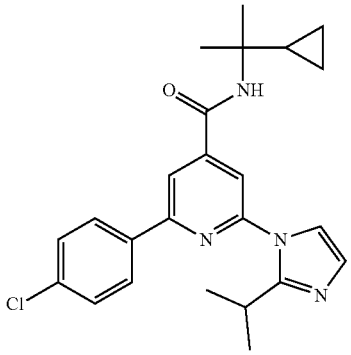 [SMILES: CC(C)c1nccn1-c1cc(C(=O)NC(C)(C)C2CC2)cc(-c2ccc(Cl)cc2)n1]

The title compound, white foam (49 mg, 46%), MS (ISP) m/z=423.2 [(M+H)⁺], was prepared in accordance with the general method of example 1 from 2-bromo-6-(4-chlorophenyl)-N-(2-cyclopropylpropan-2-yl)-pyridine-4-carboxamide (intermediate 4) (98.4 mg, 0.25 mmol) and commercially available 2-isopropyl-1H-imidazole (55.1 mg, 500 μmol).

Example 16

2-(4-Chlorophenyl)-6-(2-cyclopropyl-imidazol-1-yl)-N-(2-cyclopropyl-propan-2-yl)-pyridine-4-carboxamide

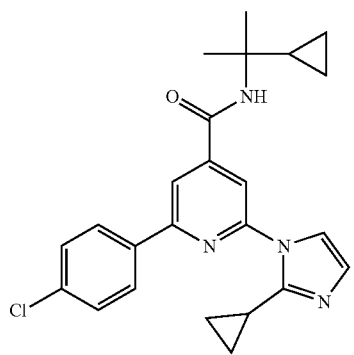 [SMILES: CC(C)(NC(=O)c1cc(-c2ccc(Cl)cc2)nc(-n2ccnc2C2CC2)c1)C1CC1]

The title compound, white foam (78 mg, 74%), MS (ISP) m/z=421.2 [(M+H)⁺], was prepared in accordance with the general method of example 1 from 2-bromo-6-(4-chlorophenyl)-N-(2-cyclopropylpropan-2-yl)-pyridine-4-carboxamide (intermediate 4) (98.4 mg, 0.25 mmol) and commercially available 2-cyclopropyl-1H-imidazole (54.1 mg, 500 μmol).

Example 17

2-(2-tert-Butylimidazol-1-yl)-6-(4-chlorophenyl)-N-(2-cyclopropyl-propan-2-yl)-pyridine-4-carboxamide

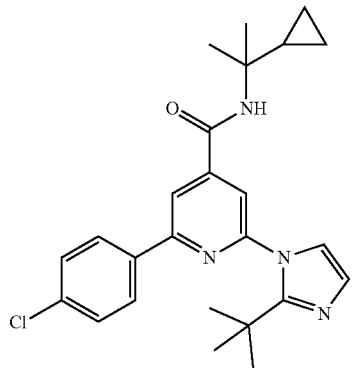 [SMILES: CC(C)(C)c1nccn1-c1cc(C(=O)NC(C)(C)C2CC2)cc(-c2ccc(Cl)cc2)n1]

The title compound, off-white foam (9 mg, 8%), MS (ISP) m/z=437.3 [(M+H)⁺], was prepared in accordance with the general method of intermediate 14 from 2-bromo-6-(4-chlorophenyl)-N-(2-cyclopropylpropan-2-yl)-pyridine-4-carboxamide (intermediate 4) (98.4 mg, 0.25 mmol) and commercially available 2-tert-butyl-1H-imidazole (37.3 mg, 300 μmol).

Example 18

N-tert-Butyl-2-(4-fluorophenyl)-6-[2-(2-hydroxypropan-2-yl)-imidazol-1-yl]-pyridine-4-carboxamide

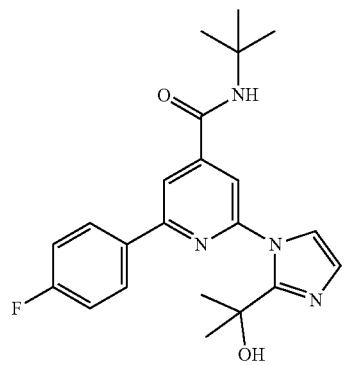 [SMILES: CC(C)(C)NC(=O)c1cc(-c2ccc(F)cc2)nc(-n2ccnc2C(C)(C)O)c1]

The title compound, off-white foam (11 mg, 11%), MS (ISP) m/z=397.2 [(M+H)$^+$], was prepared in accordance with the general method of intermediate 14 from 2-bromo-N-tert-butyl-6-(4-fluorophenyl)-pyridine-4-carboxamide (intermediate 1) (87.8 mg, 0.25 mmol) and commercially available 2-(1H-imidazol-2-yl)-propan-2-ol (37.8 mg, 300 μmol).

Example 19

N-tert-Butyl-2-(2-tert-butylimidazol-1-yl)-6-[4-(trifluoromethyl)-phenyl]-pyridine-4-carboxamide

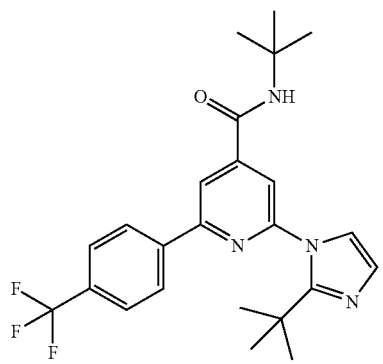 [SMILES: CC(C)(C)NC(=O)c1cc(-c2ccc(C(F)(F)F)cc2)nc(-n2ccnc2C(C)(C)C)c1]

The title compound, light brown foam (49 mg, 44%), MS (ISP) m/z=445.3 [(M+H)$^+$], was prepared in accordance with the general method of intermediate 14 from 2-bromo-N-tert-butyl-6-[4-(trifluoromethyl)-phenyl]-pyridine-4-carboxamide (intermediate 3) (100 mg, 0.25 mmol) and commercially available 2-tert-butyl-1H-imidazole (37.3 mg, 300 μmol).

Example 20

N-tert-Butyl-2-(2-cyclopropyl-imidazol-1-yl)-6-[4-(trifluoromethyl)-phenyl]-pyridine-4-carboxamide

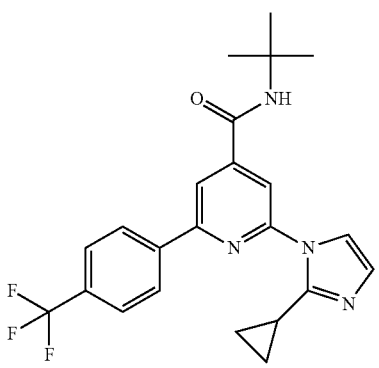 [SMILES: CC(C)(C)NC(=O)c1cc(-c2ccc(C(F)(F)F)cc2)nc(-n2ccnc2C2CC2)c1]

The title compound, off-white foam (77 mg, 72%), MS (ISP) m/z=429.2 [(M+H)$^+$], was prepared in accordance with the general method of example 1 from 2-bromo-N-tert-butyl-6-[4-(trifluoromethyl)-phenyl]-pyridine-4-carboxamide (intermediate 3) (100 mg, 0.25 mmol) and commercially available 2-cyclopropyl-1H-imidazole (54.1 mg, 500 μmol).

Example 21

N-tert-Butyl-2-(2-methyl-imidazol-1-yl)-6-[4-(trifluoromethyl)-phenyl]-pyridine-4-carboxamide

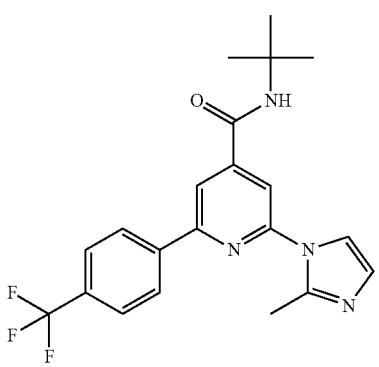 [SMILES: Cc1nccn1-c1cc(C(=O)NC(C)(C)C)cc(-c2ccc(C(F)(F)F)cc2)n1]

The title compound, off-white foam (83 mg, 83%), MS (ISP) m/z=403.2 [(M+H)$^+$], was prepared in accordance with the general method of example 1 from 2-bromo-N-tert-butyl-6-[4-(trifluoromethyl)-phenyl]-pyridine-4-carboxamide (intermediate 3) (100 mg, 0.25 mmol) and commercially available 2-methyl-1H-imidazole (41.1 mg, 500 μmol).

Example 22

N-tert-Butyl-2-(4-chlorophenyl)-6-[2-(hydroxymethyl)-imidazol-1-yl]-pyridine-4-carboxamide

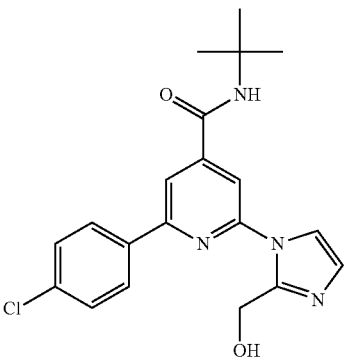 [SMILES: CC(C)(C)NC(=O)c1cc(-c2ccc(Cl)cc2)nc(-n2ccnc2CO)c1]

The title compound, white foam (66 mg, 69%), MS (ISP) m/z=385.2 [(M+H)$^+$], was prepared in accordance with the general method of example 1 from 2-bromo-N-tert-butyl-6-(4-chlorophenyl)-pyridine-4-carboxamide (intermediate 2) (91.9 mg, 250 µmol) and commercially available (1H-imidazol-2-yl)-methanol (49.1 mg, 500 µmol).

Example 23

2-(4-Chlorophenyl)-6-(2-propan-2-yl-imidazol-1-yl)-N-(1,1,1-trifluoro-2-methylpropan-2-yl)-pyridine-4-carboxamide

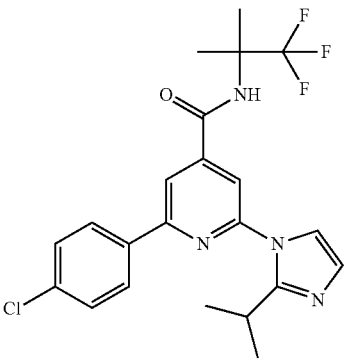 [SMILES: CC(C)c1nccn1-c1cc(C(=O)NC(C)(C)C(F)(F)F)cc(-c2ccc(Cl)cc2)n1]

The title compound, white foam (63 mg, 56%), MS (ISP) m/z=451.2 [(M+H)$^+$], was prepared in accordance with the general method of example 1 from 2-bromo-6-(4-chlorophenyl)-N-(1,1,1-trifluoro-2-methylpropan-2-yl)-pyridine-4-carboxamide (intermediate 5) (105 mg, 0.25 mmol) and commercially available 2-isopropyl-1H-imidazole (55.1 mg, 500 µmol).

Example 24

2-(4-Chlorophenyl)-6-(2-cyclopropyl-imidazol-1-yl)-N-(1,1,1-trifluoro-2-methylpropan-2-yl)-pyridine-4-carboxamide

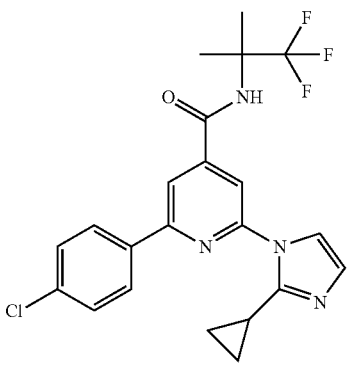 [SMILES: CC(C)(NC(=O)c1cc(-c2ccc(Cl)cc2)nc(-n2ccnc2C2CC2)c1)C(F)(F)F]

The title compound, off-white foam (77 mg, 69%), MS (ISP) m/z=449.2 [(M+H)$^+$], was prepared in accordance with the general method of example 1 from 2-bromo-6-(4-chlorophenyl)-N-(1,1,1-trifluoro-2-methylpropan-2-yl)-pyridine-4-carboxamide (intermediate 5) (105 mg, 0.25 mmol) and commercially available 2-cyclopropyl-1H-imidazole (54.1 mg, 500 µmol).

Example 25

2-(2-tert-Butylimidazol-1-yl)-6-(4-chlorophenyl)-N-(1,1,1-trifluoro-2-methylpropan-2-yl)-pyridine-4-carboxamide

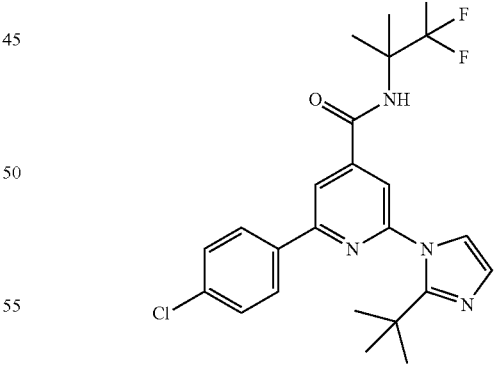

The title compound, light brown solid (70 mg, 60%), MS (ISP) m/z=465.2 [(M+H)$^+$], mp 225° C., was prepared in accordance with the general method of intermediate 14 from 2-bromo-6-(4-chlorophenyl)-N-(1,1,1-trifluoro-2-methylpropan-2-yl)-pyridine-4-carboxamide (intermediate 5) (105 mg, 0.25 mmol) (intermediate 3) (100 mg, 0.25 mmol) and commercially available 2-tert-butyl-1H-imidazole (62.1 mg, 500 µmol).

Example 26

N-tert-Butyl-2-(2-tert-butyl-imidazol-1-yl)-6-(3,4-difluorophenyl)-pyridine-4-carboxamide

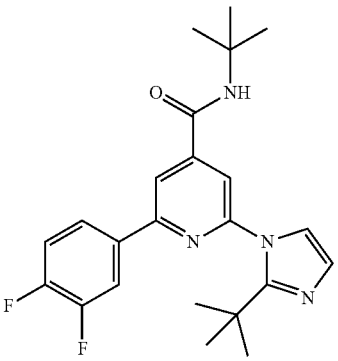

The title compound, light brown solid (45 mg, 44%), MS (ISP) m/z=413.2 [(M+H)$^+$], mp 244° C., was prepared in accordance with the general method of intermediate 14 from 2-bromo-N-tert-butyl-6-(3,4-difluorophenyl)-pyridine-4-carboxamide (intermediate 8) (92.3 mg, 0.25 mmol) (intermediate 3) (100 mg, 0.25 mmol) and commercially available 2-tert-butyl-1H-imidazole (62.1 mg, 500 μmol).

Example 27

N-tert-Butyl-2-(2-tert-butyl-imidazol-1-yl)-6-(4-methylphenyl)-pyridine-4-carboxamide

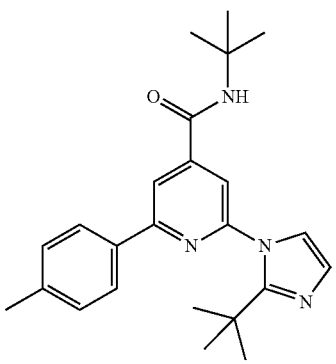 [SMILES: Cc1ccc(-c2cc(C(=O)NC(C)(C)C)cc(-n3ccnc3C(C)(C)C)n2)cc1]

The title compound, light yellow solid (59 mg, 60%), MS (ISP) m/z=391.3 [(M+H)$^+$], mp 232° C., was prepared in accordance with the general method of intermediate 14 from 2-bromo-N-tert-butyl-6-(4-methylphenyl)-pyridine-4-carboxamide (intermediate 11) (86.8 mg, 0.25 mmol) (intermediate 3) (100 mg, 0.25 mmol) and commercially available 2-tert-butyl-1H-imidazole (62.1 mg, 500 μmol).

Example 28

N-tert-Butyl-2-(2-tert-butyl-imidazol-1-yl)-6-(4-cyclopropyl-phenyl)-pyridine-4-carboxamide

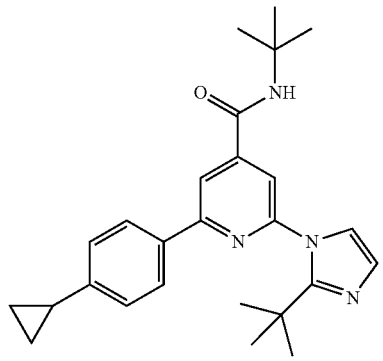 [SMILES: CC(C)(C)NC(=O)c1cc(-c2ccc(C3CC3)cc2)nc(-n2ccnc2C(C)(C)C)c1]

The title compound, light brown solid (59 mg, 57%), MS (ISP) m/z=417.3 [(M+H)$^+$], mp 226° C., was prepared in accordance with the general method of intermediate 14 from 2-bromo-N-tert-butyl-6-(4-cyclopropyl-phenyl)-pyridine-4-carboxamide (intermediate 12) (93.3 mg, 0.25 mmol) (intermediate 3) (100 mg, 0.25 mmol) and commercially available 2-tert-butyl-1H-imidazole (62.1 mg, 500 μmol).

Example 29

N-tert-Butyl-2-(2-tert-butyl-imidazol-1-yl)-6-(4-fluoro-3-methyl-phenyl)-pyridine-4-carboxamide

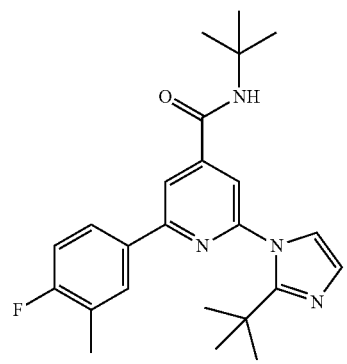

The title compound, off-white foam (50 mg, 49%), MS (ISP) m/z=409.3 [(M+H)$^+$], was prepared in accordance with the general method of intermediate 14 from 2-bromo-N-tert-butyl-6-(4-fluoro-3-methylphenyl)-pyridine-4-carboxamide (intermediate 13) (91.3 mg, 0.25 mmol) (intermediate 3) (100 mg, 0.25 mmol) and commercially available 2-tert-butyl-1H-imidazole (62.1 mg, 500 μmol).

Example 30

2-(4-Chlorophenyl)-N-(1-hydroxy-2-methylpropan-2-yl)-6-(2-propan-2-yl-imidazol-1-yl)-pyridine-4-carboxamide

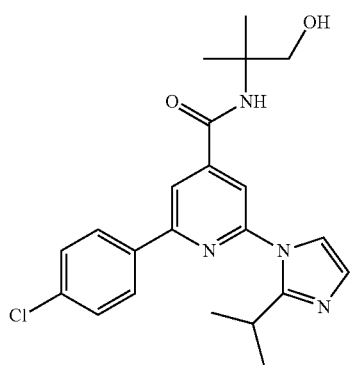 [SMILES: CC(C)c1nccn1-c1cc(C(=O)NC(C)(C)CO)cc(-c2ccc(Cl)cc2)n1]

The title compound, white foam (42 mg, 51%), MS (ISP) m/z=413.2 [(M+H)$^+$], was prepared in accordance with the general method of example 1 from 2-bromo-6-(4-chlorophenyl)-N-(1-hydroxy-2-methylpropan-2-yl)-pyridine-4-carboxamide (intermediate 7) (77.0 mg, 0.20 mmol) and commercially available 2-isopropyl-1H-imidazole (44.2 mg, 400 µmol).

Example 31

N-tert-Butyl-2-(2-tert-butyl-imidazol-1-yl)-6-(4-methoxy-phenyl)-pyridine-4-carboxamide

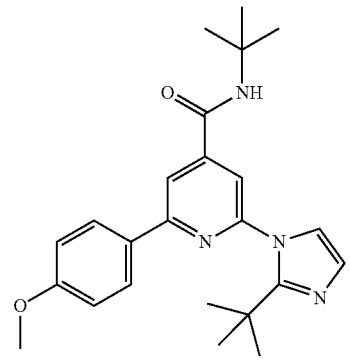 [SMILES: COc1ccc(-c2cc(C(=O)NC(C)(C)C)cc(-n3ccnc3C(C)(C)C)n2)cc1]

The title compound, light brown solid (97 mg, 95%), MS (ISP) m/z=407.3 [(M+H)$^+$], mp 235° C., was prepared in accordance with the general method of intermediate 1, step B, from 2-bromo-N-tert-butyl-6-(2-tert-butylimidazol-1-yl)-pyridine-4-carboxamide (intermediate 14) (94.8 mg, 0.25 mmol) and commercially available (4-methoxy-phenyl)-boronic acid (45.6 mg, 300 µmol).

Example 32

N-tert-Butyl-2-(2-tert-butyl-imidazol-1-yl)-6-(4-cyano-phenyl)-pyridine-4-carboxamide

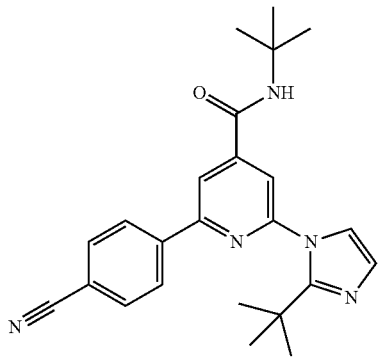 [SMILES: CC(C)(C)NC(=O)c1cc(-c2ccc(C#N)cc2)nc(-n2ccnc2C(C)(C)C)c1]

The title compound, light brown solid (99 mg, 99%), MS (ISP) m/z=402.2 [(M+H)$^+$], mp 245° C., was prepared in accordance with the general method of intermediate 1, step B, from 2-bromo-N-tert-butyl-6-(2-tert-butylimidazol-1-yl)-pyridine-4-carboxamide (intermediate 14) (94.8 mg, 0.25 mmol) and commercially available (4-cyano-phenyl)-boronic acid (44.1 mg, 300 µmol).

Example 33

N-tert-Butyl-2-(4-chlorophenyl)-6-[2-(2-hydroxy-propan-2-yl)-imidazol-1-yl]-pyridine-4-carboxamide

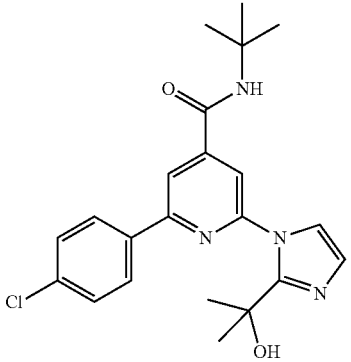 [SMILES: CC(C)(C)NC(=O)c1cc(-c2ccc(Cl)cc2)nc(-n2ccnc2C(C)(C)O)c1]

The title compound, white foam (25 mg, 24%), MS (ISP) m/z=413.2 [(M+H)$^+$], was prepared in accordance with the general method of intermediate 14 from N-tert-butyl-2-(4-chlorophenyl)-6-iodopyridine-4-carboxamide (intermediate 15) (104 mg, 0.25 mmol) and commercially available 2-(1H-imidazol-2-yl)-propan-2-ol (37.8 mg, 300 µmol).

Example 34

N-tert-Butyl-2-[2-(2-hydroxypropan-2-yl)-imidazol-1-yl]-6-[4-(trifluoromethyl)-phenyl]-pyridine-4-carboxamide

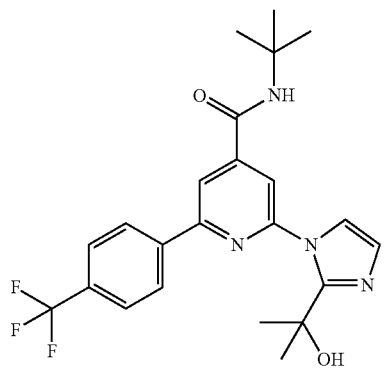 [SMILES: CC(C)(C)NC(=O)c1cc(-c2ccc(C(F)(F)F)cc2)nc(-n2ccnc2C(C)(C)O)c1]

The title compound, white foam (20 mg, 18%), MS (ISP) m/z=447.3 [(M+H)+], was prepared in accordance with the general method of intermediate 14 from N-tert-butyl-2-iodo-6-[4-(trifluoromethyl)-phenyl]-pyridine-4-carboxamide (intermediate 16) (112 mg, 0.25 mmol) and commercially available 2-(1H-imidazol-2-yl)-propan-2-ol (37.8 mg, 300 μmol).

Example 35

2-(4-Chlorophenyl)-N-(2-cyclopropylpropan-2-yl)-6-[2-(2-hydroxypropan-2-yl)-imidazol-1-yl]-pyridine-4-carboxamide

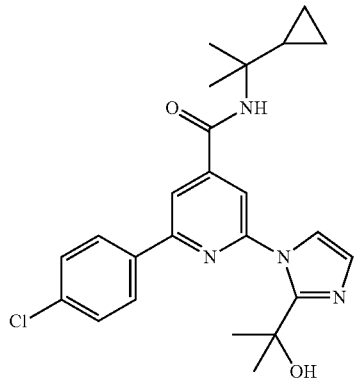 [SMILES: CC(C)(O)c1nccn1-c1cc(C(=O)NC(C)(C)C2CC2)cc(-c2ccc(Cl)cc2)n1]

The title compound, white foam (45 mg, 24%), MS (ISP) m/z=439.3 [(M+H)+], was prepared in accordance with the general method of intermediate 14 from 2-(4-chlorophenyl)-N-(2-cyclopropylpropan-2-yl)-6-iodopyridine-4-carboxamide (intermediate 17) (190 mg, 0.43 mmol) and commercially available 2-(1H-imidazol-2-yl)-propan-2-ol (65.1 mg, 517 μmol).

Example 36

2-(4-Chlorophenyl)-6-[2-(2-hydroxypropan-2-yl)-imidazol-1-yl]-N-(1,1,1-trifluoro-2-methylpropan-2-yl)-pyridine-4-carboxamide

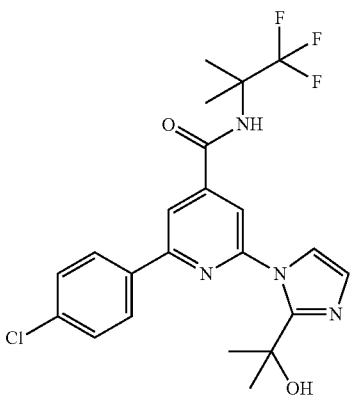 [SMILES: CC(C)(O)c1nccn1-c1cc(C(=O)NC(C)(C)C(F)(F)F)cc(-c2ccc(Cl)cc2)n1]

The title compound, white foam (32 mg, 21%), MS (ISP) m/z=467.3 [(M+H)+], was prepared in accordance with the general method of intermediate 14 from 2-(4-chlorophenyl)-6-iodo-N-(1,1,1-trifluoro-2-methylpropan-2-yl)-pyridine-4-carboxamide (intermediate 18) (150 mg, 0.32 mmol) and commercially available 2-(1H-imidazol-2-yl)-propan-2-ol (48.4 mg, 384 μmol).

Example 37

2-(2-tert-Butylimidazol-1-yl)-6-(4-chlorophenyl)-N-(2-cyanopropan-2-yl)-pyridine-4-carboxamide

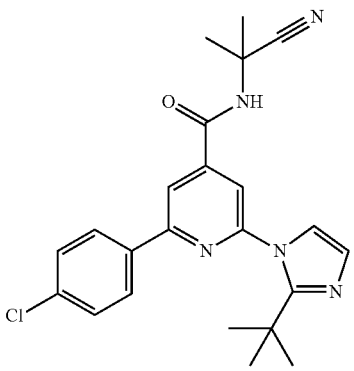 [SMILES: CC(C)(C#N)NC(=O)c1cc(-c2ccc(Cl)cc2)nc(-n2ccnc2C(C)(C)C)c1]

The title compound, off-white foam (4 mg, 4%), MS (ISP) m/z=422.2 [(M+H)+], was prepared in accordance with the general method of intermediate 14 from 2-(4-chlorophenyl)-N-(2-cyanopropan-2-yl)-6-iodopyridine-4-carboxamide (intermediate 19) (91.3 mg, 0.25 mmol) (intermediate 3) (100 mg, 0.25 mmol) and commercially available 2-tert-butyl-1H-imidazole (62.1 mg, 500 μmol).

Example 38

(RS)-2-(4-Fluorophenyl)-N-(3-methyl-1,1-dioxothi-olan-3-yl)-6-(2-propan-2-ylimidazol-1-yl)-pyridine-4-carboxamide

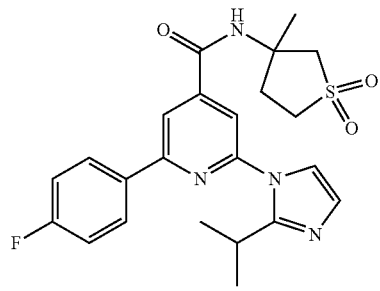 [SMILES: CC(C)c1nccn1-c1cc(C(=O)NC2(C)CCS(=O)(=O)C2)cc(-c2ccc(F)cc2)n1]

The title compound, off-white foam (57 mg, 50%), MS (ISP) m/z=457.3 [(M+H)⁺], was prepared in accordance with the general method of example 1 from (RS)-2-bromo-6-(4-fluorophenyl)-N-(3-methyl-1,1-dioxothiolan-3-yl)-pyridine-4-carboxamide (intermediate 20) (107 mg, 0.25 mmol) and commercially available 2-isopropyl-1H-imidazole (55.1 mg, 500 μmol).

Example 39

2-(4-Fluorophenyl)-N-(2-methylbutan-2-yl)-6-(2-propan-2-ylimidazol-1-yl)-pyridine-4-carboxamide

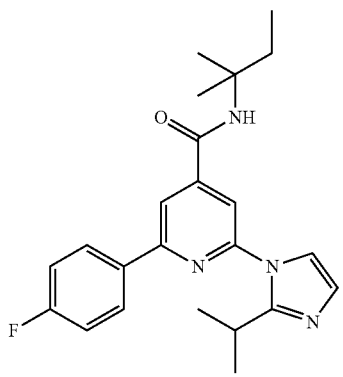 [SMILES: CCC(C)(C)NC(=O)c1cc(-c2ccc(F)cc2)nc(-n2ccnc2C(C)C)c1]

The title compound, white foam (62 mg, 63%), MS (ISP) m/z=395.2 [(M+H)⁺], was prepared in accordance with the general method of example 1 from 2-bromo-6-(4-fluorophenyl)-N-(2-methylbutan-2-yl)-pyridine-4-carboxamide (intermediate 21) (91.3 mg, 0.25 mmol) and commercially available 2-isopropyl-1H-imidazole (55.1 mg, 500 μmol).

Example 40

2-(4-Chlorophenyl)-N-(2-cyanopropan-2-yl)-6-(2-propan-2-yl-imidazol-1-yl)-pyridine-4-carboxamide

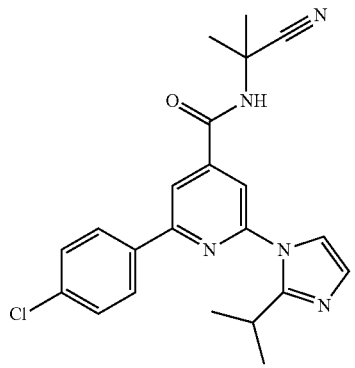 [SMILES: CC(C)c1nccn1-c1cc(C(=O)NC(C)(C)C#N)cc(-c2ccc(Cl)cc2)n1]

The title compound, off-white foam (10.5 mg, 7%), MS (ISP) m/z=408.2 [(M+H)⁺], was prepared in accordance with the general method of example 1 from 2-(4-chlorophenyl)-N-(2-cyanopropan-2-yl)-6-iodopyridine-4-carboxamide (intermediate 19) (159 mg, 374 μmol) and commercially available 2-isopropyl-1H-imidazole (82.3 mg, 747 μmol).

We claim:
1. A compound of formula I

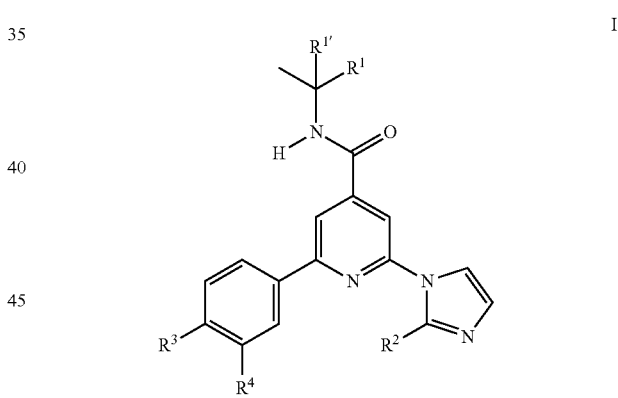

wherein $R^{1'}$ is CH₃;

$R^1$ is methyl, ethyl, CF₃, CH₂OH, cyclopropyl or cyano, or $R^{1'}$ and $R^1$ may form together a 1,1-dioxo-tetrahydro-thiophen-3-yl ring;

$R^2$ is hydrogen, methyl, ethyl, isopropyl, tert-butyl, cyclopropyl, hydroxymethyl, or 2-propyl-2-ol;

$R^3$ is Cl, F, CF₃, methyl, methoxy, isopropyl, cyano or cyclopropyl;

$R^4$ is hydrogen, methyl, F or Cl;

or a pharmaceutically acceptable salt or acid addition salt, a racemic mixture, a mixture of enantiomers or an enantiomer and/or optical isomer and/or stereoisomer thereof.

2. The compound of claim 1 of formula IA,

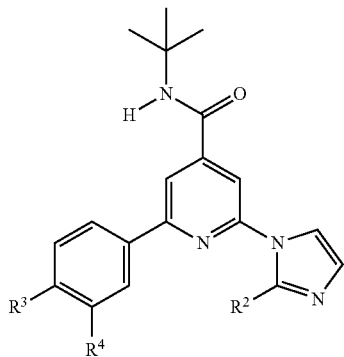

IA wherein
R² is hydrogen, methyl, ethyl, isopropyl, tert-butyl, cyclopropyl, hydroxmethyl, or
2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt thereof.

3. The compound of formula IA according to claim 2, wherein the compounds is selected from the group consisting of:
N-tert-Butyl-2-(4-chlorophenyl)-6-(2-propan-2-yl-imidazol-1-yl)-pyridine-4-carboxamide;
N-tert-Butyl-2-(4-fluorophenyl)-6-(2-propan-2-yl-imidazol-1-yl)-pyridine-4-carboxamide;
N-tert-Butyl-2-(2-propan-2-yl-imidazol-1-yl)-6-[4-(trifluoromethyl)-phenyl]-pyridine-4-carboxamide;
N-tert-Butyl-2-(2-cyclopropyl-imidazol-1-yl)-6-(4-fluorophenyl)-pyridine-4-carboxamide;
N-tert-Butyl-2-(4-chlorophenyl)-6-(2-cyclopropyl-imidazol-1-yl)-pyridine-4-carboxamide;
N-tert-Butyl-2-(4-fluorophenyl)-6-imidazol-1-yl-pyridine-4-carboxamide;
N-tert-Butyl-2-(4-fluorophenyl)-6-(2-methyl-imidazol-1-yl)-pyridine-4-carboxamide;
N-tert-Butyl-2-(2-ethyl-imidazol-1-yl)-6-(4-fluorophenyl)-pyridine-4-carboxamide;
N-tert-Butyl-2-(4-chlorophenyl)-6-imidazol-1-yl-pyridine-4-carboxamide;
N-tert-Butyl-2-(4-chlorophenyl)-6-(2-methyl-imidazol-1-yl)-pyridine-4-carboxamide;
N-tert-Butyl-2-(4-chlorophenyl)-6-(2-ethyl-imidazol-1-yl)-pyridine-4-carboxamide;
N-tert-Butyl-2-(2-tert-butyl-imidazol-1-yl)-6-(4-chlorophenyl)-pyridine-4-carboxamide;
N-tert-Butyl-2-(2-tert-butyl-imidazol-1-yl)-6-(4-fluorophenyl)-pyridine-4-carboxamide;
N-tert-Butyl-2-(4-fluorophenyl)-6-[2-(hydroxymethyl)-imidazol-1-yl]-pyridine-4-carboxamide;
N-tert-Butyl-2-(4-fluorophenyl)-6-[2-(2-hydroxypropan-2-yl)-imidazol-1-yl]-pyridine-4-carboxamide;
N-tert-Butyl-2-(2-tert-butylimidazol-1-yl)-6-[4-(trifluoromethyl)-phenyl]-pyridine-4-carboxamide;
N-tert-Butyl-2-(2-cyclopropyl-imidazol-1-yl)-6-[4-(trifluoromethyl)-phenyl]-pyridine-4-carboxamide;
N-tert-Butyl-2-(2-methyl-imidazol-1-yl)-6-[4-(trifluoromethyl)-phenyl]-pyridine-4-carboxamide;
N-tert-Butyl-2-(4-chlorophenyl)-6-[2-(hydroxymethyl)-imidazol-1-yl]-pyridine-4-carboxamide;
N-tert-Butyl-2-(2-tert-butyl-imidazol-1-yl)-6-(3,4-difluorophenyl)-pyridine-4-carboxamide;
N-tert-Butyl-2-(2-tert-butyl-imidazol-1-yl)-6-(4-methyl-phenyl)-pyridine-4-carboxamide;
N-tert-Butyl-2-(2-tert-butyl-imidazol-1-yl)-6-(4-cyclopropyl-phenyl)-pyridine-4-carboxamide;
N-tert-Butyl-2-(2-tert-butyl-imidazol-1-yl)-6-(4-fluoro-3-methyl-phenyl)-pyridine-4-carboxamide;
N-tert-Butyl-2-(2-tert-butyl-imidazol-1-yl)-6-(4-methoxy-phenyl)-pyridine-4-carboxamide;
N-tert-Butyl-2-(2-tert-butyl-imidazol-1-yl)-6-(4-cyanophenyl)-pyridine-4-carboxamide;
N-tert-Butyl-2-(4-chlorophenyl)-6-[2-(2-hydroxypropan-2-yl)-imidazol-1-yl]-pyridine-4-carboxamide; and;
N-tert-Butyl-2-[2-(2-hydroxypropan-2-yl)-imidazol-1-yl]-6-[4-(trifluoromethyl)-phenyl]-pyridine-4-carboxamide, or, a pharmaceutically acceptable acid addition salt thereof.

4. The compound according to claim 1 of formula IB,

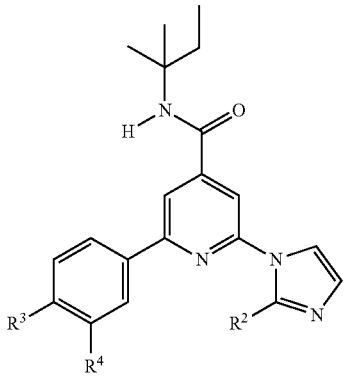

IB wherein
R² is hydrogen, methyl, ethyl, isopropyl, tert-butyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt thereof.

5. The compound of formula IB according to claim 4, wherein the compound is: 2-(4-Fluorophenyl)-N-(2-methylbutan-2-yl)-6-(2-propan-2-ylimidazol-1-yl)-pyridine-4-carboxamide; or, a pharmaceutically acceptable salt or acid addition salt thereof.

6. The compound of formula IC, according to claim 1

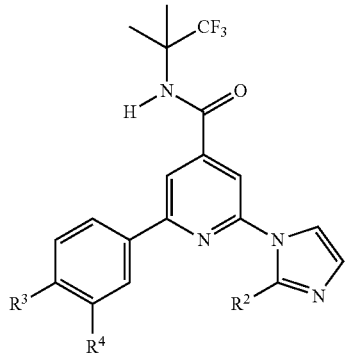

IC wherein
R² is hydrogen, methyl, ethyl, isopropyl, tert-butyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt thereof.

7. The compound according to claim 6 of formula IC wherein the compounds are:
2-(4-Chlorophenyl)-6-(2-propan-2-yl-imidazol-1-yl)-N-(1,1,1-trifluoro-2-methylpropan-2-yl)-pyridine-4-carboxamide;
2-(4-Chlorophenyl)-6-(2-cyclopropyl-imidazol-1-yl)-N-(1,1,1-trifluoro-2-methylpropan-2-yl)-pyridine-4-carboxamide;
2-(2-tert-Butylimidazol-1-yl)-6-(4-chlorophenyl)-N-(1,1,1-trifluoro-2-methylpropan-2-yl)-pyridine-4-carboxamide; or,
2-(4-Chlorophenyl)-6-[2-(2-hydroxypropan-2-yl)-imidazol-1-yl]-N-(1,1,1-trifluoro-2-methylpropan-2-yl)-pyridine-4-carboxamide;
or a pharmaceutically acceptable salt or acid addition salt thereof.

8. The compound of formula ID according to claim 1

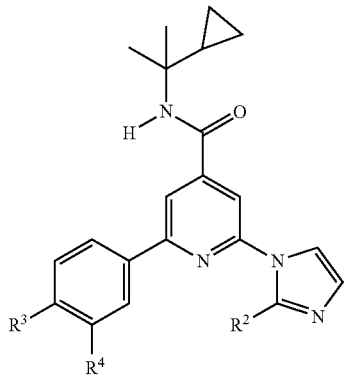

ID wherein
R² is hydrogen, methyl, ethyl, isopropyl, tert-butyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt thereof.

9. The compound according to claim 8 of formula ID wherein the compound is;
;2-(4-Chlorophenyl)-N-(2-cyclopropylpropan-2-yl)-6-(2-propan-2-yl-imidazol-1-yl)-pyridine-4-carboxamide;
2-(4-Chlorophenyl)-6-(2-cyclopropyl-imidazol-1-yl)-N-(2-cyclopropyl-propan-2-yl)-pyridine-4-carboxamide;
2-(2-tert-Butylimidazol-1-yl)-6-(4-chlorophenyl)-N-(2-cyclopropyl-propan-2-yl)-pyridine-4-carboxamide; or,
2-(4-Chlorophenyl)-N-(2-cyclopropylpropan-2-yl)-6-[2-(2-hydroxypropan-2-yl)-imidazol-1-yl]-pyridine-4-carboxamide;
or a pharmaceutically acceptable salt thereof.

10. The compound according to claim 1 of formula IE

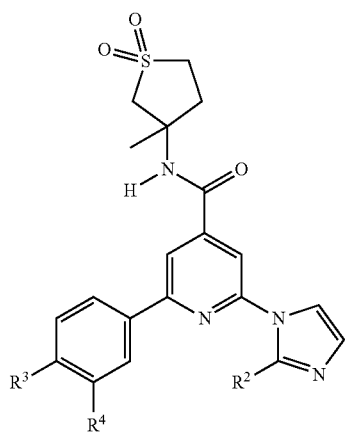

IE wherein
R² is hydrogen, methyl, ethyl, isopropyl, tert-butyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt, a racemic mixture, mixture of enantiomers or its corresponding enantiomer and/or optical isomer and/or stereoisomer thereof.

11. The compound according to claim 10 of formula IE wherein the compound is:
(RS)-2-(4-Fluorophenyl)-N-(3-methyl-1,1-dioxothiolan-3-yl)-6-(2-propan-2-ylimidazol-1-yl)-pyridine-4-carboxamide;
or a pharmaceutically acceptable salt or acid addition salt, a racemic mixture, or its corresponding enantiomer, mixture of enantiomers and/or stereoisomer thereof.

12. The compound according to claim 1 of formula IF

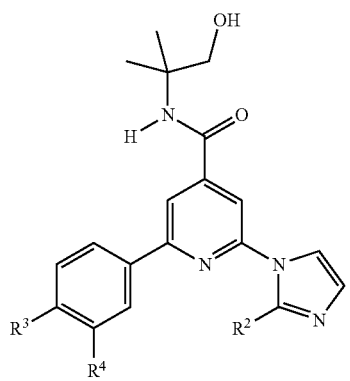

IF wherein
R² is hydrogen, methyl, ethyl, isopropyl, tert-butyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt.

13. The compound according to claim 12 of formula IF 2-(4-Chlorophenyl)-N-(1-hydroxy-2-methylpropan-2-yl)-6-(2-propan-2-yl-imidazol-1-yl)-pyridine-4-carboxamide; or, a pharmaceutically acceptable acid addition salt thereof.

14. The compound according to claim 1 of formula IG

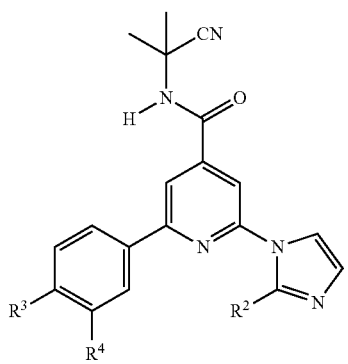

IG wherein
R² is hydrogen, methyl, ethyl, isopropyl, tert-butyl, cyclopropyl, hydroxmethyl, or 2-propyl-2-ol;
R³ is Cl, F, CF₃, methyl, methoxy, isopropyl, cyano or cyclopropyl;
R⁴ is hydrogen, methyl, F or Cl;
or a pharmaceutically acceptable salt or acid addition salt thereof.

15. The compound according to 14, wherein the compound is:
2-(2-tert-Butylimidazol-1-yl)-6-(4-chlorophenyl)-N-(2-cyanopropan-2-yl)-pyridine-4-carboxamide; or;

2-(4-Chlorophenyl)-N-(2-cyanopropan-2-yl)-6-(2-propan-2-yl-imidazol-1-yl)-pyridine-4-carboxamide.

16. A process for the manufacture of a compound of formula I according to claim 1, which process comprises the step of reacting a compound of formula II

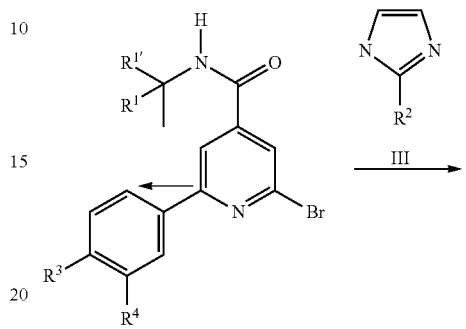

II

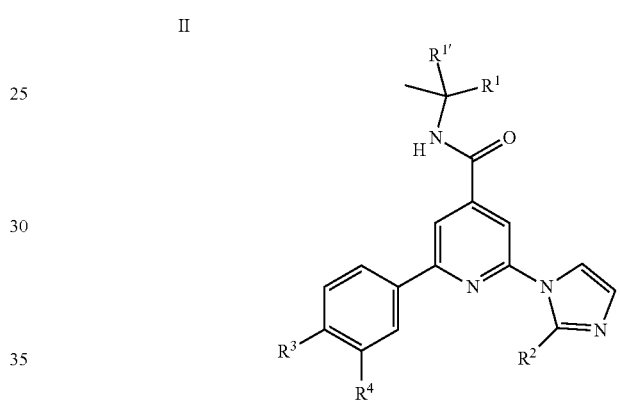

I with a compound of formula III to a compound of formula I, and, if desired, converting the compounds obtained into pharmaceutically acceptable acid addition salts.

17. A process for the manufacture of a compound of formula I according to claim 1, which process comprises the step of reacting a compound of formula IV

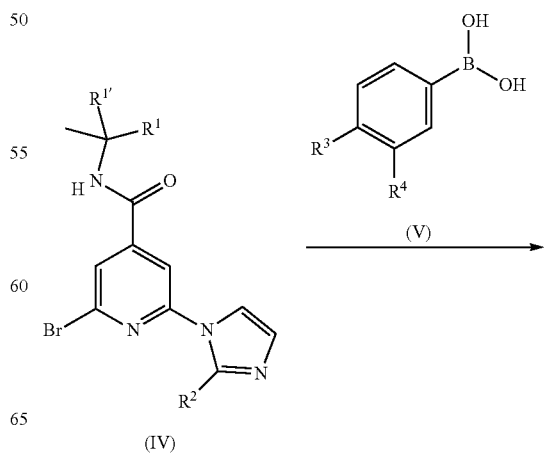

(IV)

-continued
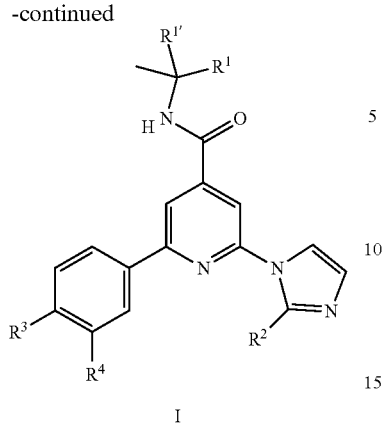
I
with a compound of formula V to a compound of formula I; and, if desired, converting the compounds obtained into pharmaceutically acceptable acid addition salts.
18. A pharmaceutical composition comprising a compound according to claim 1 and at least one pharmaceutically acceptable carrier, diluent or excipients.
* * * * *